US012697317B2

(12) United States Patent
Wang Rears et al.

(10) Patent No.: US 12,697,317 B2
(45) Date of Patent: Aug. 4, 2026

(54) DOSAGES AND USES OF ORNITHINE PHENYLACETATE FOR TREATING HYPERAMMONEMIA

(71) Applicants:AMALIVE LIMITED, Cambridge (GB); MALLINCKRODT ENTERPRISES LLC, Bedminster, NJ (US)

(72) Inventors: Xiaofeng Wang Rears, Boston, MA (US); Jack Tseng, New York, NY (US); Carmen Mak, Hampton, NJ (US); Nagaraju Poola, Belle Mead, NJ (US); Regis Vilchez, Chicago, IL (US); Aniruddha Potnis, King of Prussia, PA (US); Susan VanMeter, Ashburn, VA (US); Jan Stange, San Diego, CA (US)

(73) Assignee: Amalive Limited, Cambridge (GB)

( * ) Notice: Subject to any disclaimer, the term of this patent is extended or adjusted under 35 U.S.C. 154(b) by 920 days.

(21) Appl. No.: 17/767,009

(22) PCT Filed: Oct. 15, 2020

(86) PCT No.: PCT/US2020/055706
§ 371 (c)(1),
(2) Date: Apr. 6, 2022

(87) PCT Pub. No.: WO2021/076709
PCT Pub. Date: Apr. 22, 2021

(65) Prior Publication Data
US 2022/0362192 A1 Nov. 17, 2022

Related U.S. Application Data

(60) Provisional application No. 63/034,602, filed on Jun. 4, 2020, provisional application No. 62/979,197, filed on Feb. 20, 2020, provisional application No. 62/965,330, filed on Jan. 24, 2020, provisional application No. 62/916,159, filed on Oct. 16, 2019.

(51) Int. Cl.
| | |
|---|---|
| *A61K 31/198* | (2006.01) |
| *A61P 1/16* | (2006.01) |
| A61K 9/00 | (2006.01) |
| A61K 9/08 | (2006.01) |

(52) U.S. Cl.
CPC ............. *A61K 31/198* (2013.01); *A61P 1/16* (2018.01); *A61K 9/0019* (2013.01); *A61K 9/08* (2013.01)

(58) Field of Classification Search
CPC .................................................. A61K 31/198
See application file for complete search history.

(56) References Cited

U.S. PATENT DOCUMENTS

| | | | |
|---|---|---|---|
| 8,173,706 | B2 | 5/2012 | Anderson et al. |
| 8,389,576 | B2 | 3/2013 | Jalan et al. |
| 8,492,439 | B2 | 7/2013 | Anderson et al. |
| 8,785,498 | B2 | 7/2014 | Anderson et al. |
| 8,946,473 | B2 | 2/2015 | Anderson et al. |
| 9,034,925 | B2 | 5/2015 | Anderson et al. |
| 9,260,379 | B2 | 2/2016 | Anderson et al. |
| 9,566,257 | B2 | 2/2017 | Jalan et al. |
| 9,604,909 | B2 | 3/2017 | Anderson et al. |
| 10,039,735 | B2 | 8/2018 | Jalan et al. |
| 10,173,964 | B2 | 1/2019 | Anderson et al. |
| 10,525,029 | B2 | 1/2020 | Jalan et al. |
| 10,550,069 | B2 | 2/2020 | Anderson et al. |
| 10,610,506 | B2 | 4/2020 | Jalan et al. |
| 10,835,506 | B2 | 11/2020 | Rose et al. |
| 11,040,021 | B2 | 6/2021 | Jalan et al. |
| 11,066,352 | B2 | 7/2021 | Pilsl et al. |
| 11,161,802 | B2 | 11/2021 | Anderson et al. |
| 11,219,611 | B2 * | 1/2022 | Wang .................. A61K 9/0053 |
| 11,266,620 | B2 | 3/2022 | Jalan et al. |
| 2010/0280119 | A1 | 11/2010 | Anderson et al. |
| 2016/0338982 | A1 | 11/2016 | Ruettimann et al. |
| 2017/0135973 | A1 * | 5/2017 | Wang .................. A61K 31/198 |

FOREIGN PATENT DOCUMENTS

| | | | |
|---|---|---|---|
| AU | 2019202311 | A1 | 5/2019 |
| MX | MX/a/2021/013526 | | 1/2022 |
| WO | WO 2006/056794 | A1 | 6/2006 |
| WO | WO 2010/115055 | A1 | 10/2010 |
| WO | WO 2010/144498 | A2 | 12/2010 |
| WO | WO 2012/048043 | A1 | 4/2012 |
| WO | WO 2016/085887 | A1 | 6/2016 |
| WO | WO2016/1721112 | * | 10/2016 |

(Continued)

OTHER PUBLICATIONS

Hassanein et al., A Randomized, Double-blind, Placebo-controlled, Single Ascending Dose Study to Evaluate the Safety and Pharmacokinetics of OCR-002 (Ornithine Phenylacetate) in Patients with Stable Hepatic Cirrhosis. Hepatol. (2011) 54(4 suppl): 934A-935A.

Hassanein et al., OCR-002 (Ornithine Phenylacetate)—A Novel Ammonia Scavenger for the Treatment of He via Pagn Production: Impact of Liver Function on Metabolism and Urinary Excretion of Pagn'. Gastroenter. (2012) 142(5 suppl): S947.

Jalan et al., L-Ornithine Phenylacetate (OP): A Novel Treatment for Hyperammonemia and Hepatic Encephalopathy, Medical Hypotheses, 2007, 69(5): 1064-1069, Elsevier Ltd.

Safadi et al., OCR-002 (Ornithine Phenylacetate) is a Potent Ammonia Scavenger as Demonstrated in Phase 2b Stop-HE Study. Hepatol. (2017) 66(1 suppl): 126A.

(Continued)

*Primary Examiner* — Rei Tsang Shiao

(74) *Attorney, Agent, or Firm* — Knobbe, Martens, Olson & Bear, LLP

(57) ABSTRACT

Embodiments of the present disclosure relate to doses of ornithine phenylacetate for treating or ameliorating hyperammonemia and the methods of administrating the same in a patient with a chronic liver disease, for example, cirrhosis. In some embodiments, the patient also has hepatic encephalopathy as a complication of the liver disease.

25 Claims, 4 Drawing Sheets

(56) References Cited

FOREIGN PATENT DOCUMENTS

| | | | |
|---|---|---|---|
| WO | WO 2017/031131 A1 | 2/2017 |
| WO | WO 2017/053613 A1 | 3/2017 |
| WO | WO 2017083758 A1 | 5/2017 |
| WO | WO 2018/208677 A1 | 11/2018 |
| WO | WO 2020/227516 A1 | 11/2020 |
| WO | WO 2021/076709 A1 | 4/2021 |
| WO | WO 2021/236522 A1 | 11/2021 |

OTHER PUBLICATIONS

Stravitz et al., Safety, Tolerability, and pharmacokinetics of L-Ornithine Phenylacetate in Patients with Acute Liver Injury/Failure and Hyperammonemia, Hepatol. (2018) 67(3): 1003-1013.

Ventura-Cots et al., Safety of ornithine phenylacetate in cirrhotic decompensated patients: an open-label, dose-escalating, single-cohort study; J Clin Gastroenter. (2013) 47(10): 881-887.

Ventura-Cots et al., Impact of Ornithine Phenylacetate 9OCR-002) in Lowering Plasma Ammonia after Upper gastrointestinal Bleeding in Cirrhotic Patients. Thera Adv Gastroenter. (2016) 9(6): 823-835.

International Search Report and Written Opinion dated Dec. 18, 2020 for International Application No. PCT/US2020/055706; 16 pages.

* cited by examiner

DOSAGES AND USES OF ORNITHINE PHENYLACETATE FOR TREATING HYPERAMMONEMIA

BACKGROUND

Acute on-chronic liver failure is manifested initially as abnormal behavior and compromised cognition. Although the onset of hepatic encephalopathy (HE) can rarely be pinpointed clinically, it is a landmark in patients with advanced liver disease. An estimated 60% to 70% of patients with cirrhosis have at least subtle signs of neurocognitive impairment, and HE is the principal diagnosis in hospitalized patients with cirrhosis. Overt HE has a prevalence of approximately 30% in the cirrhotic population and accounts for approximately 150,000 patients being hospitalized annually in the United States. Severe HE in patients with cirrhosis is associated with a mortality of more than 50% in the first year alone.

Hepatic encephalopathy is a neuropsychiatric disorder that occurs when gut-derived toxins, primarily ammonia, bypass a failing liver, which would normally detoxify such agents; these toxins enter the circulation and cross the blood-brain barrier, resulting in impairment of neurotransmission and central nervous system function. Hepatic encephalopathy can arise in the setting of acute liver failure, chronic progressive liver disease in the context of advanced liver cirrhosis (overt HE), and/or as a result of portocaval shunting with or without liver disease. The pathogenesis of HE has been incompletely understood but the increase in venous ammonia concentrations remains central to our understanding of HE supporting the need for novel, safe, and effective venous ammonia-lowering therapies to treat as well as to prevent episodes of HE.

Dietary protein restriction had long been advocated as a strategy to indirectly reduce circulating venous ammonia in patients with cirrhosis. However, recent data have shown that this strategy is not effective in preventing HE and may harm these patients by making them more prone to muscle wasting.

Current treatment guidelines for the treatment of patients with episodic overt HE recommend administration of the non-absorbed disaccharides, lactulose, at a dose of 25 mL twice daily as first line agent, adjusted for the production of 3 bowel movements daily. Rifaximin, which alters gut microbiota, is approved for reduction in risk of overt HE recurrence.

L-ornithine L-aspartate (hereafter referred to as LOLA) is available as an IV product in Europe and Asia and may benefit patients by trapping circulating venous ammonia in the form of glutamine, although benefit in acute liver failure was not demonstrable. Phenylacetic acid and its prodrug, phenylbutyrate, have been used successfully to reduce ammonia in patients with genetic urea cycle disorders who have very high circulating glutamine levels. The approach of using only phenylacetic acid or phenylbutyrate to reduce high venous ammonia loads is not expected to work as effectively in patients with chronic liver disease because these patients typically have lower circulating glutamine levels (reduced expression of glutamine synthetase), although recent data of oral prophylaxis to prevent recurrent HE with glycerol phenylbutyrate have shown promising results. Additionally, the risk of chronic treatment and sustained glutamine depletion in cirrhotic patients with poor lean muscle mass remains a concern. As such, there remains a need for alternative and effective treatment of HE in patients with chronic liver diseases, for example, cirrhosis.

SUMMARY

Some embodiments of the present disclosure relate to a method of treating or ameliorating hyperammonemia in a patient in need thereof, comprising: administering a first amount of ornithine phenylacetate to the patient during a first period of time; and administering a second amount of ornithine phenylacetate to the patient during a second period of time; wherein the first amount of ornithine phenylacetate is between about 10 g to about 30 g, and the second amount of ornithine phenylacetate is less than the first amount.

Some embodiments of the present disclosure relate to a method of treating or ameliorating hyperammonemia in a patient in need thereof, comprising: selecting a patient in need of treatment of hyperammonemia who is suffering from impaired or reduced renal function, wherein said patient has an estimated glomerular filtration rate (eGFR) equal or less than 30 mL/min/1.73 m$^2$; administering a first amount of ornithine phenylacetate to the patient during a first period of time; and administering a second amount of ornithine phenylacetate to the patient during a second period of time; wherein the first amount of ornithine phenylacetate is between about 5 g to about 20 g, and the second amount of ornithine phenylacetate is less than the first amount. In some embodiments, the patient has an eGFR between 15 mL/min/1.73 m$^2$ and 29 mL/min/1.73 m$^2$.

Additional embodiments of the present disclosure relate to a method of treating or ameliorating hyperammonemia in a patient in need thereof, comprising: determining the renal function or receiving information on the renal function of a patient who is in need of treatment of hyperammonemia; and administering a first amount of ornithine phenylacetate to the patient during a first period of time; wherein the first amount is from about 10 g to about 30 g when the patient's estimated glomerular filtration rate (eGFR) is greater than 30 mL/min/1.73 m$^2$ or the estimated creatinine clearance is greater than 35 mL/min; or administering a first amount of ornithine phenylacetate to the patient during a first period of time; wherein the first amount is from about 5 g to about 20 g when the patient's estimated glomerular filtration rate (eGFR) is equal to or less than 30 mL/min/1.73 m$^2$ or the estimated creatinine clearance is equal to or less than 35 mL/min.

Some embodiments of the present disclosure relate to a method of treating or ameliorating hyperammonemia in a patient in need thereof, comprising: determining the body weight or body size or receiving information on the body weight or body size of a patient who is in need of treatment of hyperammonemia; administering a first amount of ornithine phenylacetate administered to the patient during a first period of time; monitoring plasma concentration of phenylacetic acid in the patient; and adjusting the first amount of ornithine phenylacetate administered to the patient during a first period of time based on the plasma concentration of phenylacetic acid.

Some embodiments of the present disclosure relate to a method of treating or ameliorating hyperammonemia in a patient in need thereof, comprising: determining the degree of hepatic impairment or receiving information on degree of hepatic impairment of a patient who is in need of treatment of hyperammonemia; administering a first amount of ornithine phenylacetate administered to the patient during a first period of time; monitoring plasma concentration of phenylacetic acid in the patient; and adjusting the first amount of ornithine phenylacetate administered to the patient during a first period of time based on the plasma concentration of phenylacetic acid.

Some embodiments of the present disclosure relate to a method of treating or ameliorating hyperammonemia in a patient in need thereof, comprising: identifying or selecting a patient having or at risk of having an acute or chronic liver disease or condition; measuring a serum ammonia level or receiving information on the serum ammonia level of the patient; and administering a first amount of ornithine phenylacetate to the patient when the patient's serum ammonia level is ≥21 µmol/L.

Some additional embodiments of the present disclosure relate to a pharmaceutical formulation comprising an aqueous solution of about 200 mg/mL to 400 mg/mL of ornithine phenylacetate and at least one pH adjusting agent, wherein the aqueous solution has a pH of at least about 5.

DETAILED DESCRIPTION

Figure 1:
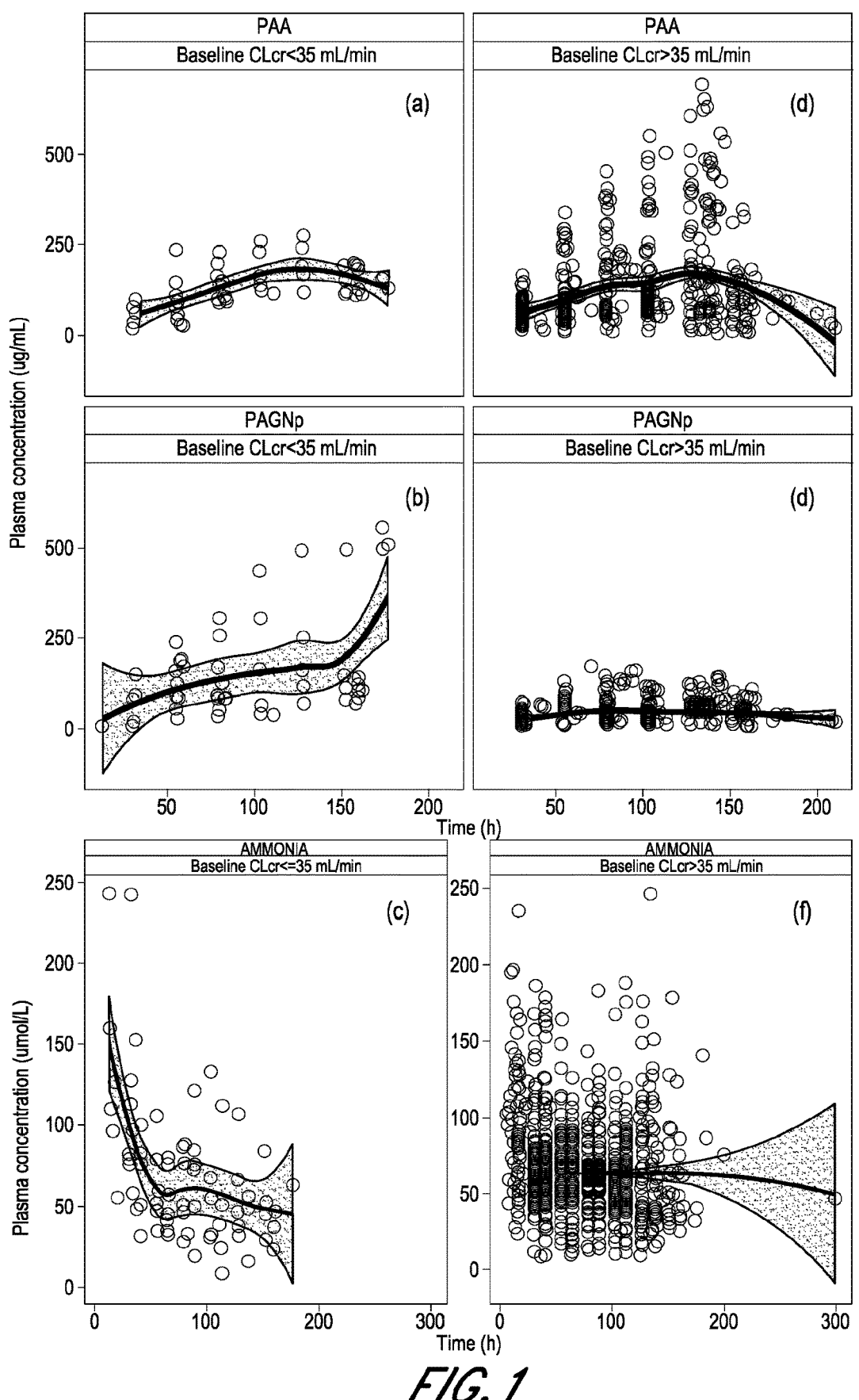
FIG. 1 shows the plasma concentration of phenylacetic acid (PAA), phenylacetylglutamine (PAGN) and ammonia exposures for the group having a baseline creatinine clearance level of less than 35 mL/min (a, b and c) as compared to the group having a baseline creatinine clearance level of greater than 35 mL/min (d, e and f) in three clinical studies (Study 2, Study 3 and Study 5 described in Example 2).

Embodiments of the present disclosure relate to methods or uses of ornithine phenylacetate to treat or ameliorate hyperammonemia and related conditions in a subject, such as one is suffering from or has suffered from one or more episodes of hepatic encephalopathy (HE). The method or use includes a dosing schedule of various amounts of ornithine phenylacetate administered during several period of time. The method or use may also include adjusting the dose(s) of ornithine phenylacetate based on one or more preexisting conditions of the subject, such as renal impairment, hepatic impairment. The method or use may also include measuring or obtain information on a patient's serum ammonia level prior to administering a first amount of ornithine phenylacetate. The method or use may further include monitoring the patient's plasma concentration of phenylacetic acid after administering a first amount of ornithine phenylacetate and making adjustment on dose(s). The method or use may include a step of selecting for treatment a patient suffering from hepatic encephalopathy due to hyperammonemia. A hepatic encephalopathy screening tool (HEST) may be used to determine whether the patient has suffered from or is suffering overt hepatic encephalopathy, such as an overt hepatic encephalopathy screening tool (O-HEST) described herein.

Additional embodiments of the present disclosure relate to pharmaceutical formulation containing ornithine phenylacetate, for example, a pharmaceutical solution containing ornithine phenylacetate and one or more pH adjusting agents for intravenous infusion.

Definitions

The section headings used herein are for organizational purposes only and are not to be construed as limiting the subject matter described.

Unless defined otherwise, all technical and scientific terms used herein have the same meaning as is commonly understood by one of ordinary skill in the art. The use of the term "including" as well as other forms, such as "include", "includes," and "included," is not limiting. The use of the term "having" as well as other forms, such as "have", "has," and "had," is not limiting. As used in this specification, whether in a transitional phrase or in the body of the claim, the terms "comprise(s)" and "comprising" are to be interpreted as having an open-ended meaning. That is, the above terms are to be interpreted synonymously with the phrases "having at least" or "including at least." For example, when used in the context of a process, the term "comprising" means that the process includes at least the recited steps, but may include additional steps. When used in the context of a compound, composition, formulation, or device, the term "comprising" means that the compound, composition, formulation, or device includes at least the recited features or components, but may also include additional features or components.

L-Ornithine phenylacetate (also referred to as LOPA or L-OPA), a L-ornithine salt of phenylacetic acid (PAA), is a novel ammonia-lowering agent that uses pathways of ammonia removal to reduce ammonia concentration in patients with varying degrees of hepatic encephalopathy (HE).

The intravenous (IV) formulation of LOPA is a fixed-dose combination therapy that allows for alternative pathways for the excretion of ammonia in the setting of cirrhosis through the enhanced elimination of ammonia through the synergistic effects of ornithine and phenylacetic acid. Ornithine stimulates the activity of glutamine synthetase, inducing body muscle to trap circulating ammonia in the form of glutamine, which is a nontoxic carrier of ammonia. Glutamine is then conjugated with phenylacetic acid to form phenylacetylglutamine (PAGN), which is excreted in urine. This strategy prevents the eventual recirculation and degradation of glutamine by glutaminase and avoids the reformation of ammonia.

As is well understood in the art, because of the experimental variability when X-ray diffraction patterns are measured on different instruments, the peak positions are assumed to be equal if the two theta (2θ) values agree to within 0.2° (i.e., ±0.2°). For example, the United States Pharmacopeia states that if the angular setting of the 10 strongest diffraction peaks agree to within ±0.2° with that of a reference material, and the relative intensities of the peaks do not vary by more than 20%, the identity is confirmed. Accordingly, peak positions within 0.2° of the positions recited herein are assumed to be identical.

The term "HEST" as described herein, refers to a set of criteria to assess the severity of a patient's HE. In some cases, HEST refers to Table A, B or C below. Details of HEST and uses thereof in connection with diagnosing a patient suffering from HE can be found in PCT Appl. No. PCT/US2020/031854, which is incorporated by reference in its entirety.

The term "OHEST" or "O-HEST" as described herein, refers to Overt Hepatic Encephalopathy Screening Tool. OHEST may be used in clinical trials evaluating treatment of HE where it is important to identify when a patient transitions from covert HE (CHE) to overt HE (OHE).

Documenting the rate of occurrence or recurrence of OHE is an important step to understanding benefit or effect of treatments. Details of OHEST and uses thereof can be found in PCT Appl. No. PCT/US2020/031854, which is incorporated by reference in its entirety.

"Treat," "treatment," or "treating," as used herein refers to administering a pharmaceutical composition/formulation for prophylactic and/or therapeutic purposes. The term "prophylactic treatment" refers to treating a patient who is not yet suffering from a disease, but who is susceptible to, or otherwise at risk of, a particular disease, whereby the treatment reduces the likelihood that the patient will develop a disease. The term "therapeutic treatment" refers to administering treatment to a patient already suffering from a disease.

Ornithine Phenylacetate Dosing Schedule

Some embodiments of the present disclosure relate to a method of treating or ameliorating hyperammonemia in a patient in need thereof, comprising: administering a first amount of ornithine phenylacetate to the patient during a first period of time; and administering a second amount of ornithine phenylacetate to the patient during a second period of time; wherein the first amount of ornithine phenylacetate is between about 10 g to about 30 g, and the second amount of ornithine phenylacetate is less than the first amount.

In some embodiments, the first period of time is from about 1 hour to about 10 hours, for example, from about 2 hours to about 9 hours, from about 3 hours to about 8 hours, from about 4 hours to about 7 hours, or from about 5 hours to about 6 hours. In one embodiment, the first period of time is about 6 hours. In some embodiments, the second period of time is longer than the first period of time. In some embodiments, the second period of time is from 12 hours to about 24 hours, or from about 16 hours to about 20 hours. In one embodiment, the second period of time is about 18 hours. In some such embodiments, a total of the first period of time and the second period of time is from about 18 hours to 36 hours, or from about 20 hours to about 30 hours. In one embodiment, the total of the first and the second period of time is about 24 hours.

In some embodiments, the first amount of ornithine phenylacetate is about 10 g, 12 g, 14 g, 16 g, 18 g, 20 g, 22 g, 24 g, 26 g, 28 g or 30 g, or a range defined by any of the two preceding values. For example, the first amount of ornithine phenylacetate may be from about 12 g to about 28 g, from about 14 g to about 26 g, from about 16 g to about 24 g, or from about 18 g to about 22 g. In one embodiment, the first amount of ornithine phenylacetate is about 20 g.

In some embodiments, the second amount of ornithine phenylacetate is about 5 g to about 25 g, for example, 5 g, 7.5 g, 10 g, 12.5 g, 15 g, 17.5, 20 g, 22.5 g or 25 g, or a range defined by any of the two preceding values. For example, the second amount of ornithine phenylacetate is from about 7.5 g to about 22.5 g, from about 10 g to about 20 g, or from about 12.5 g to about 17.5 g. In one embodiment, the second amount of ornithine phenylacetate is about 15 g.

In some embodiments, the second amount of ornithine phenylacetate is administered immediately after the completion of the administration of the first amount of ornithine phenylacetate. In some other embodiments, the second amount of ornithine phenylacetate is administered shortly after the completion of the administration of the first amount of ornithine phenylacetate, for example, within 5 minutes, 10 minutes, 15 minutes, 20 minutes, 25 minutes, 30 minutes, 35 minutes, 40 minutes, 45 minutes, 50 minutes, 55 minutes, 1 hour, 1.5 hour or 2 hours from the completion of the administration of the first amount.

The first amount of ornithine phenylacetate may be administered via different routes, for example, intravenous, oral, intraperitoneal, etc. In some embodiments, the first amount of ornithine phenylacetate is administered by intravenous infusion. In one embodiment, the first amount of ornithine phenylacetate is administered by continuous intravenous infusion for 6 hours.

The second amount of ornithine phenylacetate may be administered via different routes, for example, intravenous, oral, intraperitoneal, etc. In some embodiments, the second amount of ornithine phenylacetate is administered by intravenous infusion. In one embodiment, the second amount of ornithine phenylacetate is administered by continuous intravenous infusion for 18 hours.

In some embodiments, the method described herein further comprises administering a third amount of ornithine phenylacetate following the completion of the administration of the second amount of ornithine phenylacetate during a third period of time. In some embodiments, the third amount of ornithine phenylacetate is administered immediately after the completion of the administration of the second amount of ornithine phenylacetate. In other embodiments, the third amount of ornithine phenylacetate is administered shortly after the completion of the administration of the second amount of ornithine phenylacetate, for example, within 5 minutes, 10 minutes, 15 minutes, 20 minutes, 25 minutes, 30 minutes, 35 minutes, 40 minutes, 45 minutes, 50 minutes, 55 minutes, 1 hour, 1.5 hour or 2 hours from the completion of the administration of the second amount.

In some embodiments, the third period of time is from about 2 days to about 10 days, for example from about 3 days to about 9 days, or from about 4 days to about 8 days. In one embodiment, the third period of time is 4 days (96 hours). In some embodiments, the third amount of ornithine phenylacetate is administered continuously during the third period of time. In other embodiments, the third amount of ornithine phenylacetate is administered in separate dosing periods within the third period of time.

In some embodiments, the third amount of ornithine phenylacetate administered per day (24 hours) is the same or less than the second amount of ornithine phenylacetate. For example, the third amount of ornithine phenylacetate is about 5 g to about 25 g, for example, 5 g, 7.5 g, 10 g, 12.5 g, 15 g, 17.5, 20 g, 22.5 g or 25 g, or a range defined by any of the two preceding values. For example, the third amount of ornithine phenylacetate is from about 7.5 g to about 22.5 g, from about 10 g to about 20 g, or from about 12.5 g to about 17.5 g. In one embodiment, the third amount of ornithine phenylacetate is about 15 g.

The third amount of ornithine phenylacetate may be administered via different routes, for example, intravenous, oral, intraperitoneal, etc. In some embodiments, the third amount of ornithine phenylacetate is administered by intravenous infusion. In one embodiment, the third amount of ornithine phenylacetate is administered by continuous intravenous infusion for 4 days (96 hours).

Method of Treating Patients with Impaired Renal Functions

Some embodiments of the present disclosure relate to a method of treating or ameliorating hyperammonemia in a patient in need thereof, comprising: selecting a patient in need of treatment of hyperammonemia who is suffering from impaired or reduced renal function, wherein said patient has an estimated glomerular filtration rate (eGFR) equal or less than 30 mL/min/1.73 m$^2$; administering a first amount of ornithine phenylacetate to the patient during a first period of time; and administering a second amount of ornithine phenylacetate to the patient during a second period of time; wherein the first amount of ornithine phenylacetate is between about 5 g to about 20 g, and the second amount of ornithine phenylacetate is less than the first amount. In some embodiments, the patient has an eGFR between 15 mL/min/1.73 m² and 29 mL/min/1.73 m². In some embodiments, the patient has a estimate creatinine clearance of equal or less than 35 mL/min.

In some embodiments, the first period of time is from about 1 hour to about 24 hours, for example, from about 2 hours to about 9 hours, from about 3 hours to about 8 hours, from about 4 hours to about 7 hours, or from about 5 hours to about 6 hours. In one embodiment, the first period of time is about 6 hours. In some embodiments, the second period of time is longer than the first period of time. In some embodiments, the second period of time is from 12 hours to about 24 hours, or from about 16 hours to about 20 hours. In one embodiment, the second period of time is about 18 hours. In some such embodiments, a total of the first period of time and the second period of time is from about 18 hours to 36 hours, or from about 20 hours to about 30 hours. In one embodiment, the total of the first and the second period of time is about 24 hours.

In some embodiments, the first amount of ornithine phenylacetate is about 5 g, 7 g, 7.5 g, 10 g, 12.5 g, 15 g, 17.5 g or 20 g, or a range defined by any of the two preceding values. For example, the first amount of ornithine phenylacetate may be from about 5 g to about 17.5 g, or from 7 g to about 12.5 g. In some embodiments, the second amount of ornithine phenylacetate is about 5 g to about 20 g, for example, 5 g, 7.5 g, 10 g, 12.5 g, 15 g, 17.5, or 20 g, or a range defined by any of the two preceding values. For example, the second amount of ornithine phenylacetate is from about 5 g to about 17.5 g or from 7 g to about 12.5 g. In some embodiments, when the first period of time is about 24 hours, the second amount of ornithine phenylacetate is eliminated or not administered.

In some embodiments, the second amount of ornithine phenylacetate is administered immediately after the completion of the administration of the first amount of ornithine phenylacetate. In some other embodiments, the second amount of ornithine phenylacetate is administered shortly after the completion of the administration of the first amount of ornithine phenylacetate, for example, within 5 minutes, 10 minutes, 15 minutes, 20 minutes, 25 minutes, 30 minutes, 35 minutes, 40 minutes, 45 minutes, 50 minutes, 55 minutes, 1 hour, 1.5 hour or 2 hours from the completion of the administration of the first amount.

The first amount of ornithine phenylacetate may be administered via different routes, for example, intravenous, oral, intraperitoneal, etc. In some embodiments, the first amount of ornithine phenylacetate is administered by intravenous infusion. In one embodiment, the first amount of ornithine phenylacetate is administered by continuous intravenous infusion for about 4 to 6 hours.

The second amount of ornithine phenylacetate may be administered via different routes, for example, intravenous, oral, intraperitoneal, etc. In some embodiments, the second amount of ornithine phenylacetate is administered by intravenous infusion. In one embodiment, the second amount of ornithine phenylacetate is administered by continuous intravenous infusion for about 12 to 18 hours.

In some embodiments, the method described herein further comprises administering a third amount of ornithine phenylacetate following the completion of the administration of the second amount of ornithine phenylacetate during a third period of time. In some embodiments, the third amount of ornithine phenylacetate is administered immediately after the completion of the administration of the second amount of ornithine phenylacetate. In other embodiments, the third amount of ornithine phenylacetate is administered shortly after the completion of the administration of the second amount of ornithine phenylacetate, for example, within 5 minutes, 10 minutes, 15 minutes, 20 minutes, 25 minutes, 30 minutes, 35 minutes, 40 minutes. 45 minutes, 50 minutes, 55 minutes, 1 hour, 1.5 hour or 2 hours from the completion of the administration of the second amount.

In some embodiments, the third period of time is from about 2 days to about 10 days, for example from about 3 days to about 9 days, or from about 4 days to about 8 days. In one embodiment, the third period of time is 4 days (96 hours). In some embodiments, the third amount of ornithine phenylacetate is administered continuously during the third period of time. In other embodiments, the third amount of ornithine phenylacetate is administered in separate dosing periods within the third period of time.

In some embodiments, the third amount of ornithine phenylacetate administered per day (24 hours) is the same or less than the second amount of ornithine phenylacetate. For example, the third amount of ornithine phenylacetate is about 5 g to about 20 g, for example, 5 g, 7 g, 7.5 g, 10 g, 12.5 g, 15 g, 17.5, or 20 g, or a range defined by any of the two preceding values. For example, the third amount of ornithine phenylacetate is from about 7.5 g to about 17.5 g, or from about 10 g to about 15 g, or from 7 g to about 12.5 g.

The third amount of ornithine phenylacetate may be administered via different routes, for example, intravenous, oral, intraperitoneal, etc. In some embodiments, the third amount of ornithine phenylacetate is administered by intravenous infusion. In one embodiment, the third amount of ornithine phenylacetate is administered by continuous intravenous infusion for 3 to 4 days (72 to 96 hours).

Method of Treating Patients with Various Doses of Ornithine Phenylacetate Based on Assessment of Renal Functions Additional embodiments of the present disclosure relate to a method of treating or ameliorating hyperammonemia in a patient in need thereof, comprising: determining the renal function or receiving information on the renal function of a patient who is in need of treatment of hyperammonemia; and administering a first amount of ornithine phenylacetate to the patient during a first period of time; wherein the first amount is from about 10 g to about 30 g when the patient's estimated glomerular filtration rate (eGFR) is greater than 30 mL/min/1.73 m² or the patient's estimated creatinine clearance level is greater than 35 mL/min; or administering a first amount of ornithine phenylacetate to the patient during a first period of time; wherein the first amount is from about 5 g to about 20 g when the patient's estimated glomerular filtration rate (eGFR) is equal to or less than 30 mL/min/1.73 m² or the patient's estimated creatinine clearance level is greater than 35 mL/min.

In some further embodiments of the methods of treating patients with impaired renal function, when the patient has severe renal impairment, the first amount of ornithine phenylacetate may be reduced by at least about 50% (e.g., about 53%) of the standard second amount of ornithine phenylacetate as described herein. In some such embodiment, the first amount of ornithine phenylacetate administered to the patient during a first period of time is from about 5 g to about 15 g, or from about 7 g to about 12.5 g, or about 10 g. In some such embodiment, the administration is by intravenous infusion. In some embodiments, the first period of time is from about 1 hour to about 24 hours, for example, from about 2 hours to about 9 hours, from about 3 hours to about 8 hours, from about 4 hours to about 7 hours, or from about 5 hours to about 6 hours. In one embodiment, the first period of time is about 6 hours. In another embodiment, the first period of time is about 24 hours.

In some further embodiments of the methods of treating patients with impaired renal function, the patient with renal impairment is further administered a second amount of ornithine phenylacetate after the administration of the first amount of omithine phenylacetate. The second amount of ornithine phenylacetate may be administered immediately or shortly after the completion of the administration of the first amount of omithine phenylacetate as described above. The second amount of ornithine phenylacetate may be administered via different routes, for example, intravenous, oral, intraperitoneal, etc. In some embodiments, the second amount of ornithine phenylacetate is administered by intravenous infusion. In one embodiment, the second amount of ornithine phenylacetate is administered by continuous intravenous infusion for about 12 to 18 hours. When the patient has severe renal impairment, the second amount of omithine phenylacetate may also be reduced by at least about 50% (e.g., about 53%) of the standard second amount of ornithine phenylacetate as described herein, for example, the reduced second amount of omithine phenylacetate may be from about 2.5 g to about 12.5 g, from about 5 g to about 10 g or about 7 g. In some further embodiment, the combined first and second period of time is about 24 hours. In some such embodiments, when the first period of time is about 24 hours, then the second amount of omithine phenylacetate is eliminated or not administered.

In some further embodiments of the methods of treating patients with impaired renal function, the patient with renal impairment is further administered a third amount of ornithine phenylacetate after the administration of the second amount of ornithine phenylacetate. The third amount of ornithine phenylacetate may be administered immediately or shortly after the completion of the administration of the second amount of ornithine phenylacetate as described above. The third amount of ornithine phenylacetate may be administered via different routes, for example, intravenous, oral, intraperitoneal, etc. In some embodiments, the third amount of ornithine phenylacetate is administered by intravenous infusion. In one embodiment, the third amount of ornithine phenylacetate is administered by continuous intravenous infusion for 3 to 4 days (72 to 96 hours). When the patient has severe renal impairment, the third amount of ornithine phenylacetate may also be reduced by at least about 50% (e.g., about 53%) of the standard third amount of ornithine phenylacetate as described herein, for example, the reduced third amount of ornithine phenylacetate may be from about 2.5 g to about 12.5 g, from about 5 g to about 10 g, or about 7 g.

Method of Treating Patients with Various Doses of Ornithine Phenylacetate Based on Assessment of Hepatic Impairment Some embodiments of the present disclosure relate to a method of treating or ameliorating hyperammonemia in a patient in need thereof, comprising: determining the degree of hepatic impairment or receiving information on degree of hepatic impairment of a patient who is in need of treatment of hyperammonemia; administering a first amount of ornithine phenylacetate administered to the patient during a first period of time; monitoring plasma concentration of phenylacetic acid in the patient; and adjusting the amount of ornithine phenylacetate administered to the patient during a second period of time based on the plasma concentration of phenylacetic acid.

In some embodiments, when the patient has severe hepatic impairment (for example, the patient with Child-Pugh C) may be subject to elevated plasma phenylacetic acid (PAA) exposure after administration of the first amount of ornithine phenylacetate. For example, for a patient with the same body weight, a patient with Child-Pugh C would be exposed to PAA at steady state about 15%, 20%, 25%, 30%, 35%, 40%, 45%, or 50% higher than that of a patient with Child-Pugh B. In some such embodiments, the elevated plasma PAA level may cause adverse events such as neurological adverse events (e.g., somnolence, fatigue, lightheadedness, headache, dysgeusia, hypoacusis, disorientation, impaired memory, peripheral neuropathy, or combination thereof). In some such embodiments, the amount of ornithine phenylacetate administered during a second period of time is reduced based on the monitored the plasma PAA level after the administration of the first amount of ornithine phenylacetate. In some further embodiments, the plasma PAA level is at a steady state at the time of measurement (for example, during infusion period). In some embodiments, the amount of ornithine phenylacetate administered during a second period of time (i.e., a second amount) is reduced by about 10%, 15%, 20%, 25%, 30%, 35%, 40%, 45%, or 50% as compared the standard second amount of ornithine phenylacetate described herein (e.g., 15 g). In some further embodiments, the amount of ornithine phenylacetate administered during a third period of time (i.e., a third amount) is also reduced by about 10%, 15%, 20%, 25%, 30%, 35%, 40%, 45%, or 50% as compared the standard third amount of ornithine phenylacetate described herein (e.g., 15 g/24 hour).

Alternatively, the method may include the following steps: determining the degree of hepatic impairment or receiving information on the degree of hepatic impairment of a patient who is in need of treatment of hyperammonemia; adjusting a first amount of ornithine phenylacetate administered to the patient during a first period of time when the subject has a Child-Pugh score of equal or greater than 10 (Class C). The method may further comprises monitoring plasma concentration of phenylacetic acid in the patient after the administration of the first amount of ornithine phenylacetate. In some such embodiments, the first amount of ornithine phenylacetate is reduced by about 10%, 15%, 20%, 25%, 30%, 35%, 40%, 45%, or 50% as compared to the standard first amount of ornithine phenylacetate described herein (e.g., about 20 g). In some further embodiments, the second and the third amounts of ornithine phenylacetate are also reduced from the standard second and third amount of ornithine phenylacetate described herein (e.g., 15 g for both second and third amount) by the similar or same percentage as described above for the first amount.

Method of Treating Patients with Various Doses of Ornithine Phenylacetate Based on Assessment of Body Weight or Body Size Some embodiments of the present disclosure relate to a method of treating or ameliorating hyperammonemia in a patient in need thereof, comprising: determining the body weight or body size or receiving information on the body weight or body size of a patient who is in need of treatment of hyperammonemia; administering a first amount of ornithine phenylacetate administered to the patient during a first period of time; monitoring plasma concentration of phenylacetic acid in the patient; and adjusting the amount of ornithine phenylacetate administered to the patient during a second period of time based on the plasma concentration of phenylacetic acid.

In some embodiments, when the body weight or body size of the patient is significantly below the standard weight/size (e.g., for an adult, the standard weight is about 70 kg), the patient may be subject to elevated plasma phenylacetic acid (PAA) exposure. In some such embodiments, the elevated plasma PAA level may cause adverse events such as neurological adverse events (e.g., somnolence, fatigue, light-headedness, headache, dysgeusia, hypoacusis, disorientation, impaired memory, peripheral neuropathy, or combination thereof). In some such embodiments, the amount of ornithine phenylacetate administered during a second period of time is reduced based on the monitored the plasma PAA level after the administration of the first amount of ornithine phenylacetate. In some further embodiments, the plasma PAA level is at a steady state at the time of measurement (for example, during infusion period). In some embodiments, the amount of ornithine phenylacetate administered during a second period of time (i.e., a second amount) is reduced by about 10%, 15%, 20%, 25%, 30%, 35%, 40%, 45%, or 50% as compared the standard second amount of ornithine phenylacetate described herein (e.g., 15 g). In some further embodiments, the amount of ornithine phenylacetate administered during a third period of time (i.e., a third amount) is also reduced by about 10%, 15%, 20%, 25%, 30%, 35%, 40%, 45%, or 50% as compared the standard third amount of ornithine phenylacetate described herein (e.g., 15 g/24 hour).

Alternatively, the method may include the following steps: determining the body weight or body size or receiving information on the body weight or body size of a patient who is in need of treatment of hyperammonemia; adjusting a first amount of ornithine phenylacetate administered to the patient during a first period of time when the subject's body weight or body size is significantly below the standard body weight or body size. The method may further comprises monitoring plasma concentration of phenylacetic acid in the patient after the administration of the first amount of ornithine phenylacetate. In some such embodiments, the subject's body weight or body size may be significantly below the standard body weight or body size if the subject is a minor child or infant. In some other such embodiments, the subject's body weight or body size may be significantly below the standard body weight or body size if the subject is underweight or has a very low BMI (e.g., having at least 25%, 30%, 35%, 40%, 45%, or 50% less weight or size than a typical 70 kg adult). In some such embodiments, the first amount of ornithine phenylacetate is reduced by 25%, 30%, 35%, 40%, 45%, or 50% as compared to the standard first amount of ornithine phenylacetate described herein (e.g., about 20 g). In some further embodiments, the second and the third amounts of ornithine phenylacetate are also reduced from the standard second and third amount of ornithine phenylacetate described herein (e.g., 15 g for both second and third amount) by the similar or same percentage as described above for the first amount.

Method of Treating Patients with Various Doses of Ornithine Phenylacetate Based on Assessment of Serum Ammonia Analysis Some embodiments of the present disclosure relate to a method of treating or ameliorating hyperammonemia in a patient in need thereof, comprising: identifying or selecting a patient having or at risk of having an acute or chronic liver disease or condition; measuring a serum ammonia level or receiving information on the serum ammonia level of the patient; and administering a first amount of ornithine phenylacetate to the patient. In some embodiments, the serum ammonia level is about, or greater than about, an upper limit of normal (ULN). In some embodiments, the serum ammonia level is about or greater than about, 15 µmol/L, 16 µmol/L, 17 µmol/L, 18 µmol/L, 19 µmol/L, 20 µmol/L, 21 µmol/L, 25 µmol/L, 30 µmol/L, 35 µmol/L, 40 µmol/L, 45 µmol/L, 50 µmol/L, 60 µmol/L, 70 µmol/L, 80 µmol/L, 90 µmol/L, 100 µmol/L, 120 µmol/L, 140 µmol/L, 160 µmol/L, 180 µmol/L or 200 µmol/L, or a range defined by any of the two preceding values. In some embodiments, the patient is suffering from or is at risk of cirrhosis. In one embodiment, the serum ammonia level of a patient suffering from cirrhosis is ≥21 µmol/L when the patient is at risk of hepatic encephalopathy or may have suffered from at least one episode of hepatic encephalopathy.

In any embodiments of the methods described herein, the method may further comprise measuring a blood ammonia level of the patient prior to administering the first amount of ornithine phenylacetate to the patient. In some cases, the patient's serum ammonia level is above a normal level. In one embodiment, the serum ammonia level of the patient is ≥21 µmol/L.

In any embodiments of the methods described herein, the patient is also receiving standard of care, for example, the patient is receiving lactulose with or without rifaximin.

In any embodiments of the methods described herein, the patient has cirrhosis. In some instances, the patient is at risk of hepatic encephalopathy or has had at least one episode of hepatic encephalopathy (HE), for example, overt HE as a complication of cirrhosis (Stage 2, 3, or 4 as defined by Hepatic Encephalopathy Staging Tool (HEST)). In some instances, the patient may be hospitalized due to one or more hepatic encephalopathy episodes. In some such cases, the patient has received at least 4 hours to 6 hours of standard of care prior to the administration of the first amount of ornithine phenylacetate.

In any embodiments of the methods described herein, ornithine phenylacetate is L-ornithine phenylacetate.

In any embodiments of the methods described herein, at least one of the first, second and third amount of ornithine phenylacetate is administered as an aqueous solution comprising about 100 mg/mL to about 500 mg/mL ornithine phenylacetate. In some embodiments, each of the first, second and third amount of ornithine phenylacetate is administered as an aqueous solution comprising about 200 mg/mL to about 400 mg/mL ornithine phenylacetate. In one embodiment, each of the first, second and third amount of ornithine phenylacetate is administered as an aqueous solution comprising about 300 mg/mL ornithine phenylacetate. In some such embodiment, the aqueous solution of ornithine phenylacetate has a pH of at least about 5, for example, a pH range from about 5.4 to about 6.5. In some embodiments, the aqueous solution of ornithine phenylacetate is stored at a temperature of about 2° C. to about 8° C. (e.g., 5° C.) prior to the administration.

In any embodiments of the methods described herein, ornithine phenylacetate may be administered via intravenous infusion. In some further embodiment ornithine phenylacetate is administered by continuous intravenous infusion. In some embodiments, the first amount of ornithine phenylacetate is administered by continuous intravenous infusion over about 6 hours; and second amount of ornithine phenylacetate is administered by continuous intravenous infusion over about 18 hours; and the third amount of ornithine phenylacetate is administered by continuous intravenous infusion over 1, 2, 3, 4 or 5 days (24, 48, 72, 96 or 120 hours). In some embodiments, the first amount of ornithine phenylacetate is about 20 g, administered by continuous intravenous infusion over about 6 hours; and second amount of ornithine phenylacetate is about 15 g, administered by continuous intravenous infusion over about 18 hours; and the third amount of ornithine phenylacetate is about 15 g/24 hour, administered by continuous intravenous infusion for 3 or 4 days (72 or 96 hours). The intravenous infusion hours and/or amount of ornithine phenylacetate may be reduced when a subject has adverse events, for example, those due to elevated plasma phenylacetic acid levels. In some embodiments, the patients has severe renal impairment, hepatic impairment, or under weight, as described herein.

Formulations of Ornithine Phenylacetate and Methods of Preparation

Additional embodiments of the present disclosure relate to a pharmaceutical formulation comprising an aqueous solution of ornithine phenylacetate. In some embodiments, the aqueous solution has a concentration of ornithine phenylacetate of about 100 mg/mL, 125 mg/mL, 150 mg/mL, 175 mg/mL, 200 mg/mL, 225 mg/mL, 250 mg/mL, 275 mg/mL, 300 mg/mL, 325 mg/mL, 350 mg/mL, 375 mg/mL, 400 mg/mL, 425 mg/mL, 450 mg/mL or 500 mg/mL, or a range defined by any two of the preceding values. For example, in some embodiments, the aqueous solution has about 200-400 mg/mL ornithine phenylacetate. In one embodiment, the aqueous solution has about 300 mg/mL ornithine phenylacetate. In some embodiments, the pharmaceutical formulation further comprises at least one pH adjusting agent. In some such embodiments, the pH adjusting agent is hydrochloric acid (HCl), citric acid, or any water soluble acidic pH adjusting agent that is suitable for a pharmaceutical formulation, or a combination thereof. In one embodiment, the pH adjusting agent is HCl. In some embodiments, the aqueous solution has a pH of at least about 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9 or 7, or a range defined by any two of the preceding values. For example, in some embodiments, the aqueous solution has a pH range of about 5.4 to about 6.5. In some embodiments, the pharmaceutical formulation is stored at room temperature. In other embodiments, the pharmaceutical formulation is stored at a temperature of about, −5° C., 0° C., 1° C., 2° C., 3° C., 4° C., 5° C., 6° C., 7° C., 8° C., 9° C., 10° C. or 15° C., or a range defined by any two of the preceding values. For example, in some embodiments, the pharmaceutical formulation is stored at a temperature from about 2° C. to 8° C. In one embodiment, the pharmaceutical formulation is stored at about 5° C. prior to the administration. In some further embodiments, the pharmaceutical formulation has a pH range of 5.4 to 6.5 (e.g., pH=5.5) at a temperature between about 2° C. to 8° C. (e.g., 5° C.).

The selection of pH range can advantageously prevent ornithine phenylacetate from precipitating out from the aqueous solution during long-term storage (e.g., between about 2° C. to 8° C.). It has been observed that when pH of the aqueous solution decreases from 5.4 to 5.3, 5.2, 5.1 or 5, varying amount of crystalline form of ornithine phenylacetate precipitated out of the aqueous solution after 12 days when the aqueous solutions were stored at about 5° C. In addition, the pH is also the main driving factor in the formation of 3-amino-2-piperidone, the lactam impurity of L-ornithine. It was observed that lactam formation slowed at lower pH values in accelerated temperature conditions during the stability study. In some embodiments, the aqueous solution of ornithine phenylacetate described herein has less than about 5%, 4%, 3%, 2%, 1%, 0.5%, 0.4%, 0.3%, 0.2% or 0.1% ornithine phenylacetate precipitate when stored for at least 2 weeks, 4 weeks, 2 months, 3 months, 6 months, or 9 months at a temperature between about 2° C. to 8° C. In some embodiments, the aqueous solution of ornithine phenylacetate described herein comprises less than about 0.5%, 0.4%, 0.3%, 0.2%, 0.1%, 0.09%, 0.08%, 0.07%, 0.06%, 0.05%, 0.04%, 0.03%, 0.02%, or 0.01% by weight of the lactam impurity 3-amino-2-piperidone for up to 3, 6 or 9 months at a storage temperature ranging from about 2° C. to about 8° C. In some further embodiments, the aqueous solution of ornithine phenylacetate described herein comprises equal or less than about 0.05% by weight of the lactam impurity 3-amino-2-piperidone for up to 6 months at a storage temperature ranging from about 2° C. to about 8° C. (e.g., 5° C.).

In some embodiments, the pharmaceutical formulation is prepared by dissolving ornithine phenylacetate in an aqueous solution. In some such embodiments, the ornithine phenylacetate is L-ornithine phenylacetate. In some further embodiments, L-ornithine phenylacetate is in a crystalline form, for example, Form II, Form I, or Form III as disclosed in U.S. Publication No. 2010/0280119, which is incorporated by reference in its entirety. Form II L-ornithine phenylacetate has an X-ray powder diffraction pattern comprising at least three characteristic peaks elected from the group consisting of approximately 6.0°, 13.9°, 14.8°, 17.1°, 17.8° and 24.1° 2θ. Form I L-ornithine phenylacetate has an X-ray powder diffraction pattern comprising at least three characteristic peaks elected from the group consisting of approximately 5.8°, 14.1°, 18.6°, 19.4°, 22.3° and 24.8° 2θ. Form III L-ornithine phenylacetate has an X-ray powder diffraction pattern comprising at least three characteristic peaks elected from the group consisting of approximately 4.9°, 13.2°, 17.4°, 20.8° and 24.4° 2θ. In some embodiments, the method further includes adding at least one pH adjusting agent to the aqueous solution. In some embodiments, the method may further includes cooling the aqueous solution.

The pharmaceutical formulation of ornithine phenylacetate may be used in any of the methods or uses described herein for treating or ameliorating hyperammonemia.

HEST and O-HEST

The following tools may be used to diagnosing a patient suffering from HE or overt HE. Tables A-C are HEST and Table D is O-HEST.

TABLE A

| | |
|---|---|
| Stage 0/1 | No asterixis* and no disorientation based on the following 5 questions (i.e., patient provides correct response to Questions 1, 2, 3, 4, and 5):<br>1. What is your name?<br>2. What city are we in?<br>3. What type of place is this? (correct answer hospital)<br>4. What is the year?<br>5. What is the month? |
| Stage 2 | Asterixis* and disorientation based on the following 5 questions, i.e., any single incorrect response qualifies the patient as Stage 2 for the following questions 1, 2, 3, 4, or 5:<br>1. What is your name?<br>2. What city are we in?<br>3. What type of place is this? (correct answer hospital)<br>4. What is the year?<br>5. What is the month? |
| Stage 3 | Stupor, arousable but falls asleep, responsive to verbal stimuli<br>Obvious confusion<br>Gross disorientation |
| Stage 4 | Coma |

*Observe for 30 seconds; 3 or more flaps in that timeframe considered positive for asterixis.

TABLE B

| Stage 0/1 | Patient to be considered Stage 0/1 if any of the following apply:<br>No asterixis*/No disorientation (i.e., correct answers to all 5 questions below)<br>No asterixis*/Yes disorientation (i.e., 1 or more incorrect answers to 5 questions below)<br>Yes asterixis*/No disorientation (i.e., correct answers to all 5 questions below)<br>1. What is your name?<br>2. What city are we in?<br>3. What type of place is this? (correct answer hospital)<br>4. What is the year?<br>5. What is the month? |
|---|---|
| Stage 2 | Patient to be considered Stage 2 if the following applies:<br>Yes asterixis */Yes disorientation (i.e., 1 or more incorrect answers to 5 questions below)<br>1. What is your name?<br>2. What city are we in?<br>3. What type of place is this? (correct answer hospital)<br>4. What is the year?<br>5. What is the month?<br>Note: patients who are sleepy, but easily arousable and responsive to questions, can qualify as HEST Stage 2 if appropriate |
| Stage 3 | Patient to be considered Stage 3 if any of the following apply:<br>Severe drowsiness (can be aroused by moderate stimuli but then almost immediately drifts back to sleep<br>Stupor (unresponsiveness from which the patient can be aroused only by vigorous and repeated stimuli; incomprehensible speech)<br>Obvious confusion/gross disorientation (inattention to questions; inappropriate response to commands or questions; bewilderment) |
| Stage 4 | Patient to be considered Stage 4 if coma is present.<br>A coma is defined as a state of unarousable unresponsiveness. |

*Observe patient for 30 seconds; 3 or more flaps in that timeframe is considered positive for asterixis

TABLE C

| Stage 0/1 | Patient to be considered Stage 0/1 if any of the following apply:<br>No Disorientation (i.e., all correct answers for questions 1 through 7)<br>Mild Disorientation (i.e., one incorrect answer for questions 1 through 7)<br>1. What is your name? |
|---|---|

TABLE C-continued

| | 2. What year were you born?<br>3. What city or town do you live in?<br>4. What type of place is this?<br>5. What is the year?<br>6. Who is the current president (or country-specific leader)?<br>7. What is the month?<br>Note: Patients who are in Stage 0/1 will be alert, responsive, and able to engage in conversation with clinical staff. |
|---|---|
| Stage 2 | Patient to be considered Stage 2 if the following applies:<br>Disorientation (i.e., two or more incorrect answers for questions 1 to 7)<br>1. What is your name?<br>2. What year were you born?<br>3. What city or town do you live in?<br>4. What type of place is this?<br>5. What is the year?<br>6. Who is the current president (or country-specific leader)?<br>7. What is the month?<br>Note: Patients who are in Stage 2 may be sleepy (though easily arousable) but will be responsive and able to engage in conversation with clinical staff, but may be slower to respond. |
| Stage 3 | Patient to be considered Stage 3 if any of the following apply:<br>Gross disorientation/obvious confusion (inappropriate response to questions or commands; bewilderment; inattention to questions)<br>Severe drowsiness (can be aroused by moderate stimuli but then almost immediately drifts back to sleep)<br>Stupor (unresponsiveness from which the patient can be aroused only by vigorous and repeated stimuli; incomprehensible speech)<br>Note: Patients who are in Stage 3 may have severe drowsiness where they can be aroused by moderate stimuli, but then almost immediately drift back to sleep. |
| Stage 4 | Patient to be considered Stage 4 if coma is present.<br>A coma is defined as a state of unarousable unresponsiveness. |

When using the OHEST, it is required that source of information for OHEST documentation be identified (e.g., clinician-observed, caregiver input, observed by outside medical professional, review of medical records, or virtual visit, etc.). Other potential causes of altered mental status (e.g., alcohol intoxication, sleep deprivation) must be reasonably ruled out before confirming an OHE event. In some instances, clinical findings should be present for at least 1 hour to be considered an OHE event.

TABLE D

Is the patient disoriented to time?
Documentation:
Knows the year
Knows the month
Knows the day of the week
Knows the date
Is the patient disoriented to place?
Documentation:
Knows the country
Knows the province/state
Knows the city/town
Knows the type of place (e.g., hospital, house)

Please select one response below that best describes the patient's level of consciousness.

| Alert and responsive (Patient is alert and can engage in conversation) | Sleepy but responsive (Patient may be slower to respond when engaged in conversation) | Severe drowsiness, lethargy, or somnolence (Patient may need repeated verbal or moderate physical stimuli to initiate a response; drifts back to sleep easily or quickly) | Stuporous (Patient can be aroused only by vigorous and repeated physical stimuli; patient likely has incomprehensible speech) | Comatose (Patient is unarousable and unresponsive to any verbal or noxious stimuli) |
|---|---|---|---|---|

If a patient answers two or more of the four "time" questions incorrectly, the patient is considered to be disoriented to time and will be documented as having an OHE event. If a patient answers one or more of the four "place" questions incorrectly, the patient is considered to be disoriented to place and will be documented as having an OHE event. People who are disoriented to place (typically viewed as more serious than disorientation to time) are generally already disoriented to time. If a patient is identified to be either "alert and responsive" or "sleepy but responsive", an OHE event has occurred ONLY if patient is disoriented to either time or place. Patients who are experiencing more severe stages of hepatic encephalopathy (i.e., Stages 3 or 4) are unlikely to engage in any meaningful conversation or be able to respond to the orientation questions. Therefore, these patients will be documented as having an OHE event based primarily on their level of consciousness ("severe drowsiness, lethargy, or somnolence", "stuporous", or "comatose"). The OHEST does not rely on the presence or absence of asterixis in the determination of HE severity.

It is understood by those of skill in the art that numerous and various modifications can be made without departing from the spirit of the present invention. Therefore, it should be clearly understood that the embodiments of the present disclosure are illustrative only and are not intended to limit the scope of the present invention. Any reference referred to herein is incorporated by reference for the material discussed herein, and in its entirety.

EXAMPLE

The example below is non-limiting and is merely representative of various aspects of the present disclosure.

Example 1

A Multicenter, Randomized, Double-Blind, Placebo-Controlled Phase 3 Study to Evaluate the Efficacy, Safety, and Tolerability of LOPA (an Intravenous Formulation of L-Ornithine Phenylacetate) in Hospitalized Patients With Cirrhosis and Hyperammonemia Associated With an Episode of Hepatic Encephalopathy.
Objectives and Endpoints
The primary objective and endpoints listed below will be evaluated for LOPA+Standard of Care (SoC) vs placebo+SoC in hospitalized patients with cirrhosis experiencing an episode of overt HE associated with hyperammonemia.

TABLE 1

| Primary Objective/Endpoints | |
| --- | --- |
| Primary Objective | Primary Efficacy Endpoint |
| To evaluate the efficacy of LOPA + SoC vs placebo + SoC with IV administration for up to 5 days to patients with hyperammonemia. | Time to clinical response, defined as the time in hours from starting therapy to a two stage improvement in HEST scale for patients with baseline Stage 3 or 4 evaluated for up to Day 5 (+3 h), or a one stage improvement for patients with baseline Stage 2 evaluated for up to Day 5 (+3 h). | h: hours; HEST: Hepatic Encephalopathy Staging Tool; IV: intravenous; SoC: Standard of Care.

The time to confirmed clinical response and time to complete response will be censored at the last time point measured in cases which a patient does not sufficiently improve. However, in the case of a death or liver transplant, this time will not be censored prior to the end of the timeframe of the endpoint, because the patient is known to not improve throughout.

The key secondary and other secondary objectives and endpoints listed below will be evaluated for LOPA+SoC vs placebo+SoC in hospitalized patients with cirrhosis experiencing an episode of overt HE associated with hyperammonemia as follows:

TABLE 2

| Key Secondary Objective/Endpoints | |
| --- | --- |
| Key Secondary Objective | Key Secondary Endpoint |
| Efficacy of LOPA + SoC vs placebo + SoC will also be assessed using a more stringent efficacy endpoint. | Time to complete response or HEST stage (0/1) from starting therapy up to Day 5 (+3 hours). |

SoC = Standard of Care; HEST: Hepatic Encephalopathy Staging Tool.

TABLE 3

| Other Secondary Objective/Endpoints | |
| --- | --- |
| Other Secondary Objectives | Other Secondary Endpoints |
| Efficacy of LOPA + SoC vs placebo + SoC will also be assessed using additional efficacy endpoints. | Mean change in HEST from Baseline at each nominal time point.<br>Percentage of patients with HEST = 0/1 score at Day 5 (+3 hours).<br>Percentage of patients with HEST = 0/1 score at Day 14 or discharge.<br>Percentage of patients with HEST = 0/1 score at 48 hours.<br>Time to readiness for hospital discharge defined as meeting criteria of hospital discharge due to resolution of OHE.<br>Percentage of patients readmitted to hospital due to an episode of OHE at Day 14 and Day 30 post discharge. |
| To evaluate the safety and tolerability of LOPA + SoC up to 1 month after treatment. | The frequency and severity of treatment emergent adverse events (TEAEs), serious adverse events (SAEs), adverse events of special interest (AESIs), discontinuation due to TEAEs, and deaths.<br>12-Lead ECG parameters.<br>Safety laboratory changes from Baseline.<br>Physical and neurological examination findings.<br>Vital sign measurements. |

AE = adverse event; EOI = end of infusion; EOT = end of treatment; OHE = Overt hepatic encephalopathy; ORN = ornithine; LD = loading dose; PAA = phenylacetic acid; PAGN = phenylacetylglutamine; SoC = Standard of Care.

TABLE 4

| Other Pre-Specified Objective/Endpoints | |
| --- | --- |
| Other Pre-specified Objectives | Other Pre-specified Endpoints |
| To evaluate venous ammonia concentrations as a PD marker with the administration of LOPA. | Venous ammonia concentrations and changes from the baseline<br>Time from treatment initiation to achieve the first venous ammonia concentrations at or below the ULN. |
| To evaluate between group differences on healthcare resource utilization and patient outcomes that are | Average hospital length of stay by treatment.<br>Percentage of patients that meet institution criteria for discharge |

TABLE 4-continued

Other Pre-Specified Objective/Endpoints

| Other Pre-specified Objectives | Other Pre-specified Endpoints |
| --- | --- |
| meaningful to hospital, health plan and care givers. | at +24 hours post final EOI by treatment. Percentage of patients admitted to ICU during the hospital stay by treatment. Average length of ICU stay by treatment. Percentage of patients re-admitted to hospital by Day 14 post discharge by treatment. Percentage of patients readmitted to hospital within 30 days post discharge by treatment. |
| To evaluate the PK of ORN, PAA, and PAGN as well as sources of variability contributing to the PK. | Population PK model and covariate effect on PK parameters. |

EOI = end of infusion; EOT = end of treatment; ICU = Intensive care unit; OHE = Overt hepatic encephalopathy; ORN = ornithine; LD = loading dose; PAA = phenylacetic acid; PAGN = phenylacetylglutamine; PK = Pharmacokinetic; SoC = Standard of Care; ULN = Upper limit of normal.

Study Design

This is a randomized, placebo-controlled, double-blind, multicenter, and superiority Phase 3 study with 2 parallel groups. Approximately 400 patients are planned for enrollment at approximately 150 study sites around the globe. The study will enroll hospitalized patients experiencing an episode of overt HE (assessed as Stage 2, 3, or 4 per the Hepatic Encephalopathy Staging Tool [HEST]) associated with hyperammonemia as a complication of cirrhosis. Patients will be randomized to 1 of 2 treatment groups:

1. LOPA+SoC.
2. Placebo+SoC.

Patients will be allocated to treatment groups in a 1:1 ratio using an interactive phone/web response system (IXRS) with randomization stratified according to 3 factors:

Rifaximin use (yes vs no).

HEST Stage 2 vs HEST Stage 3 and Stage 4.

Child-Pugh (C-P) class C vs A and B.

Lactulose±rifaximin as Standard of Care (SoC) treatment for overt HE should be administered per the clinical judgement of the investigator and usual institutional practice. Patients can be located anywhere in the hospital according to medical condition and usual clinical triage (ie, patients need not be located in a particular unit, such as the intensive care unit to participate in this study; any hospitalized setting, including the emergency department, is acceptable).

Up to 50% of the patients will be allowed to receive rifaximin as part of the SoC. Conditions of rifaximin inclusion are as follows:

Patients who initiate or alter rifaximin treatment within 10 days of screening will be excluded.

Patients that did not receive any dose of rifaximin within 10 days prior to screening can start rifaximin as part of their treatment for HE. For these patients, rifaximin should be started at the same time as initiation of study treatment on Day 1.

An Independent data and safety monitoring board (IDSMB) will review unblinded safety data and PAA/PAGN concentrations, neurological examinations, ammonia concentrations, and adverse events (AEs) (including central nervous system (CNS) AEs) when approximately 10% (±40) of patients have completed treatment or about 6 months have elapsed since first patient enrolled, whichever occurs first. A second review may occur approximately 6 months later during the first year. The IDSMB will continue to monitor the safety data on additional patients enrolled on an annual basis, as requested by the sponsor, or as determined by the IDSMB.

The study will comprise the following study periods:

Screening/Randomization/Baseline Period. After patients diagnosed as having overt HE have received a minimum of 6 hours of SoC treatment with lactulose±rifaximin (provided dose was not initiated nor altered within 10 days prior to screening), screening activities may be initiated, starting with written informed consent. The Screening and Baseline assessments should be completed as rapidly as possible so that patients may begin receiving study treatment as soon as possible and within approximately 24 hours from the time of overt HE diagnosis. During screening, assessments and procedures will be performed and information will be collected to determine study eligibility and to establish the patient's baseline information. After completion of all screening procedures, patients will be randomized to treatment.

Treatment Period. Patients will be randomized 1:1 to receive either LOPA+SoC or placebo+SoC for up to 5 days (120 hours). The following dosing regimen is planned for this study:

First 24 hours of treatment (0 to less than 24 hours)

Loading Dose (LD): 6 hour IV infusion containing 20 g of LOPA+SoC or placebo+SoC (0 to 6 hours).

Intermediate Dose: 18 hour IV infusion containing 15 g LOPA+SoC or placebo+SoC (6 to 24 hours) immediately following the initial LD.

Remainder of treatment (not less than 24 hours to not more than 120 hours)

Maintenance Dose: for up to 4 days (from 24 hours up to 120 hours) continuous IV infusions of 15 g LOPA+SoC or placebo+SoC at a rate of 15 g per 24 hours.

The start of infusion time will be Time 0 (Day 1) and will continue through 120 hours (Day 5). The treatment period will include efficacy, safety, and PK assessments. The infusion must be stopped at least 3 hours before discharge from the hospital. Therefore, patients who are discharged from the hospital before Day 5 (120 hours) of continuous study treatment (as medically appropriate) will not receive the full 120 hours of intended treatment. End of treatment (EOT) assessments will be performed after the end of the last infusion. The last assessment should be performed within 3 hours after the end of the last infusion (±1 hour). All patients are expected to complete end-of-treatment (EOT) assessments (including those who did not receive the full 120 hours of intended treatment).

For safety, venous ammonia concentrations and PAA concentrations will be monitored while the patient is receiving study drug treatment. An independent unblinded medical monitor will review PAA and ammonia concentration data on an ongoing basis. The independent unblinded medical monitor may notify the sponsor of the need to convene an ad hoc safety review meeting with the IDSMB as outlined in the Safety Monitoring Plans.

A minimum of 216 patients with Child-Pugh Class A or B achieving clinical response by end of treatment (EOT) are required for the primary analysis to achieve 85% power; therefore, enrollment of at least 360 (180 per group) patients with Child-Pugh Class A or B is anticipated for this study. Up to an additional 40 patients with Child-Pugh Class C will also be enrolled to explore the safety and efficacy of study treatment in this patient population. While the total sample size for this study is estimated to be 400, the study may continue enrollment beyond 400 until 216 clinical events are observed in the Child-Pugh A and B population.

The duration of the study from first patient first visit to last patient last visit will be dependent on the ability of the study sites to identify and enroll eligible patients. The entire study is expected to require approximately 30 to 36 months to complete from the time the first patient is randomized.

Follow Up Period. After completion of the EOT assessments, patients will enter the Follow-Up (F/U) Period of this study for up to 30 days. The F/U Period includes safety assessments. All patients will return to the study site for two F/U Visits, which will occur on Day 14 (±2 days) and Day 30 (±2 days).

For patients who are still hospitalized for 24 hours or more post final EOI, additional safety and efficacy assessments will be performed at 2 time points: 24 hours post final EOI and at the time of pre-discharge from the hospital, as applicable.

Patients may participate in the study for a total of up to approximately 5 weeks. Patient participation in the study will be considered complete after the last follow-up assessment has been completed. The study includes a Screening/Baseline/Randomization Period of up to 24 hours, a 5-day Treatment Period (up to 120 hours or EOT), and a 30-day Follow Up (F/U) period.

Inclusion Criteria

During the Screening Period (except at noted below), each patient must meet all of the following criteria to be enrolled in this study:

1. Written informed consent from the patient or caregiver must be obtained before any screening assessments are performed. Patient or caregiver must be adequately informed of and understand the nature and risks of the study. If consent cannot be expressed in writing by the patient, a caregiver or appropriate legal representative must provide consent for the patient to participate according to local regulations.

2. Be ≥18 and ≤80 years of age at Screening Visit and can be male or female.

3. Known or evident liver cirrhosis. Diagnosis of liver cirrhosis may be based on clinical, radiological, and or histological criteria, including 1 or more of the following:
   a. Previous histologic diagnosis on liver biopsy; e.g., Metavir Score of >3 (including ¾ or 3-4), Ishak score of >4 or
   b. Clinical evidence of cirrhosis, defined as aspartate aminotransferase>alanine aminotransferase (ie, AST>ALT), platelet count <150,000, and nodular liver surface on computed tomography (CT) scan or magnetic resonance imaging (MRI); or
   c. Clinical evidence of significant portal hypertension, based on current or history of gastroesophageal varices on endoscopy, evidence of portosystemic collaterals (on contrast CT or MRI with contrast), and/or presence of ascites; or
   d. Transient elastography consistent with cirrhosis, i.e., result of >13.0 kPa.

4. Hospitalized patient experiencing an episode of overt HE as a complication of cirrhosis. Note that eligible patients may be already admitted to the hospital (possibly for an unrelated diagnosis) or awaiting admittance from the emergency department.

5. Hyperammonemia at Screening, defined as elevated venous ammonia concentration >ULN at local laboratory.

6. Women of childbearing potential (WOCBP) must have a negative urine pregnancy test at Screening. A serum pregnancy test will be performed to confirm pregnancy if a urine pregnancy test result is positive; confirmation must be obtained prior to randomization to study drug.

7. Overt HE episode defined as ≥Stage 2 (HEST) throughout the Screening Period, including the pre-randomization HEST assessment.
   Notes: At the end of the Screening Period, despite receiving lactulose (±rifaximin if treatment not initiated or altered within 10 days prior to overt HE diagnosis) as SoC treatment for HE as appropriate for at least 6 hours+2 hours maximum, patients must still be clearly overtly encephalopathic with HEST remaining ≥Stage 2 during screening procedures and at the pre-randomization assessment.

8. Model for End stage Liver Disease (MELD) Score ≤25.

Exclusion Criteria

Patients meeting any of the following criteria (during the Screening Period, except as noted below) will be excluded from the study:

1. Is a clinical site employee (temporary, part time, full time, etc.) or a family member of the research staff conducting the study, or of the sponsor, or of the contract research organization, or of the institutional review board (IRB)/independent ethics committee (IEC).

2. Has a life expectancy <5 weeks. Patients with malignancy (e.g., hepatocellular carcinoma) need not be excluded if they exceed this life expectancy.

3. Has hyponatremia, defined as blood sodium level ≤125 mmol/L.

4. Has severe renal impairment, end-stage renal disease, or acute kidney failure at time of Screening. A patient must be excluded from the study if either of the following criteria are met:
   eGFR ≤30 mL/min/1.73 $m^2$.
   Need for any method of blood filtration for kidney failure (e.g., hemodialysis, peritoneal dialysis, continuous venovenous hemofiltration).
   Note: Patients with eGFR ≤30 mL/min/1.73 $m^2$ can participate with approval of the sponsor's medical monitor of the study only after results from ongoing study in this population indicate it is appropriate.

5. Has New York Heart Association Class 3 or Class 4 congestive heart failure, or overt clinical signs of congestive heart failure.

6. A patient requiring mechanical ventilation may be permitted to enroll if intubation is elective and only for airway protection (i.e., to prevent aspiration) due to severe HE and ongoing sedation is not required. Transitory intubation with sedation for a specific procedure or intervention, anticipated to be <24 hours, is permitted. With the intention of excluding patients requiring intubation for respiratory failure or severe pneumonia, ventilator usage in the following settings would render a patient ineligible:
   Fraction of inspired oxygen (FiO2)>0.5 (>50% oxygen).
   Positive end-expiratory pressure (PEEP)>10 cm $H_2O$ (water).

Note: Continuous positive airway pressure is permitted.

7. Has a history of prior cerebrovascular accident with residual cognitive sequelae.

8. Has schizophrenia, dementia, or other severe psychiatric disorders that would interfere with evaluation of HE using HEST.

9. Presents to the hospital with acute alcohol or drug intoxication (patients with alcoholic liver disease/cirrhosis due to alcohol, but not currently inebriated, are allowed). Inebriated patients and those with acute effects of alcohol at presentation, by immediate prior history, overall clinical evaluation, or blood alcohol level ≥1.6 g/L (0.16% w/v, 160 mg/dL, 34.74 mmol/L) will be excluded, unless blood alcohol level returns to undetectable levels during the Screening Period, and there are no signs of acute withdrawal or alcohol related encephalopathy. Patients with symptoms of serious alcohol withdrawal at either screening or baseline are excluded.

10. Patients with gastrointestinal bleeding will be excluded if any of the following occur at the time of Screening:

Continued blood transfusion is required for active and uncontrolled gastrointestinal bleeding; and/or The investigator considers the patient likely to die of gastrointestinal bleeding.

Notes: Patients with bleeding due solely to portal hypertensive gastropathy may be enrolled, provided that they do not meet exclusion criterion #10, specified above. Patients with a transjugular intrahepatic portosystemic shunt (TIPS) are permitted in this study.

11. Has hemodynamic instability, defined as a meeting any of the following:

Mean arterial pressure of <60 mm Hg;

Evidence of poor organ perfusion; or

Use of more than 1 vasopressor to support blood pressure.

Note: Use of terlipressin, vasopressin (and analogs), and octreotide (and somatostatin analogs) to address complex vascular dynamic issues specific to this population (eg, variceal bleeding, renal perfusion) is permitted. However, if >1 vasopressor is being given for hemodynamic support of unstable mean arterial pressure—implying shock and sequelae—the patient will be excluded.

12. Concomitant administration of drugs known to interfere with renal excretion of PAGN, such as probenecid.

13. Use of Molecular Adsorbent Recirculating System (MARS).

14. Currently receiving, or expectation that the patient will receive, any of the following: L-ornithine L-aspartate (LOLA/Hepa Merz®), sodium benzoate, Ammonul®, sodium phenylbutyrate (Buphenyl®), glycerol phenylbutyrate (Ravicti®), or any other medication/therapy prohibited per Section 6.5.2 (eg, sedatives, drugs that cause hyperammonemia).

15. Participation in another interventional, investigational experimental device or novel drug clinical trial within 30 days prior to admission throughout the duration of the study. Trials of established medications (not for HE) or new techniques must be reviewed case-by-case by the medical monitor.

Note: Observational studies are allowed.

16. Is listed as high priority candidate for liver transplantation, ie, "Status 1" per United Network for Organ Sharing definition, or for whom the investigator anticipates imminent liver transplantation within 5 days.

17. Is a prior transplant recipient (solid organ, bone marrow, or stem cell).

18. Has irreversible brain damage, massive aspiration pneumonia, and/or non-hepatic encephalopathic causes for significant altered mental status, as determined by the investigator, i.e., sepsis.

19. Has known or suspected hypersensitivity or allergic reaction to ORN, PAA, or any component of LOPA.

20. If female, is pregnant or breastfeeding.

21. Has any other clinically significant disease, disorder, or laboratory abnormality, or situation, which, in the opinion of the investigator, might put the patient at risk due to participation in the study, or may influence the results of the study or the patient's ability to complete the study.

22. Has any of the following laboratory abnormalities at the Screening Visit:

Hemoglobin no more than 8.0 g/dL.

Platelet count no more than 25,000 cells/µL.

Absolute neutrophil count no more than 1000 cells/µL.

23. Patient has initiated or altered doses of rifaximin treatment within 10 days of Screening.

Example 2. Exposure of Phenyl Acetic Acid (PAA) and Phenylacetylglutamine (PAGN) In Different Subpopulations and Their Correlation with Adverse Events This example summarizes various clinical studies of intravenous administration of L-ornithine phenylacetate (LOPA) in both healthy subjects and subjects with varying degrees of cirrhosis.

Clinical Studies and Analysis Methods

PK and AE data from five clinical studies are described below:

Study 1: Two intravenous administration dosages of LOPA were administered to healthy subjects: (a) a single ascending dose (SAD); and (b) a multiple ascending dose (MAD). The tested doses in SAD were 1 g, 10 g, 20 g and 30 g with 4 hours of infusion, and 30 g, 40 g, and 60 g with 24 hours of infusion. The tested doses in MAD were 1 g, 3 g, 10 g, and 20 g with 24 hours of infusion administered for 5 days.

Study 2: A SAD study was conducted in patients with stable cirrhosis [Child-Pugh A (C-P A), n=31; Child-Pugh B (C-P B), n=12)] to evaluate the tolerability and PK of LOPA. Doses of 1 g, 3 g, 10 g, and 20 g with 4 hours of intravenous infusion, and 10 g, 20 g, and 40 g with 24 hours of intravenous infusion were tested.

Study 3: A Phase 2b, placebo-controlled, randomized, double-blind clinical study to evaluate the safety, PK, and efficacy of LOPA in hospitalized patients with liver cirrhosis (C-P A, n=3; C-P B, n=66; C-P C, n=132), hyperammonemia, and an acute episode of HE was conducted. Either LOPA or placebo was administered to patients as a continuous intravenous infusion for up to 5 days together with standard of care. Dosage was per baseline calculation of hepatic synthetic and portal elements, 4-6 points: 20 g/24 h; 7-9 points: 15 g/24 h; and 10-12 points: 10 g/24 h.

Study 4: An open-label study assessed the PK and safety of LOPA in healthy Chinese Han and Japanese subjects. The dose selected for the study was 20 g with 24 hours of intravenous infusion.

Study 5: An open-label study assessed the PK and safety following the intravenous administration of LOPA in adults with severe renal impairment. Seven subjects with severe renal impairment and seven age, sex, and weight-matched subjects with normal renal function participated, wherein 5 males and 2 females participated in both groups. The mean ages and weights were similar between normal renal function and severe renal impairment groups (62 yrs vs 59.1 yrs; and 87.7 kg vs 84.8 kg, respectively). Subjects with normal renal function (CLcr at baseline ≥90 mL/min) received a single IV infusion of 15 g/24 hour; subjects with severely impaired renal function (eGFR at baseline from 15 to 29 mL/min/1.73 $m^2$) received a reduced dose of 7 g/24 hours.

Pharmacokinetics Analysis

Rich blood samples to obtain complete PK profiles of ORN, PAA, and PAGN were collected in Studies 1, 2, 4 and 5, and only sparse PK samples were collected in Study 3. Plasma concentrations of ORN, PAA, PAGN, and urine concentrations of PAGN were measured using a validated LC-MS/MS method.

Both non-compartmental analysis and population PK analysis were conducted to identify factors attributing to the PK of PAA, ORN, and PAGN. Ethnicity factor on the PK of PAA was explored using the PK data from Caucasian, Chinese, and Japanese healthy subjects in Studies 1 and 4. Hepatic dysfunction on PAA PK was investigated using the PK data from patients in Studies 2 and 3. Renal dysfunction on PAA and PAGN plasma exposure was explored using the PK data from Studies 2, 3 and 5.

Adverse Events Assessment

Adverse events (AEs) were assessed and coded using the Medical Dictionary for Regulatory Activities (MedDRA) preferred term and system organ class. AEs of special interest (AESIs) for LOPA included somnolence, fatigue, lightheadedness, headache, dysgeusia, hypoacusis, disorientation, impaired memory, and peripheral neuropathy.

AE and PAA/PAGN Exposure Relationship

The evaluation of potential correlation between central nervous system (CNS) AEs and PAA exposure was conducted on data from Studies 1-3. The first reported drug-related CNS AE was included in the analysis. For each such CNS AE, two PAA concentrations were identified based on the time of onset of the AE and the time of PAA assessment: (1) the closest PAA concentration before the onset of the AE; and (2) the closest PAA concentrations after the onset of the AR All time points were calculated relative to the start of study drug infusion.

Renal dysfunction is expected to elevate PAGN plasma concentrations. AE data from subjects with severe renal impairment were summarized. In addition, comparisons of PAA, PAGN plasma concentrations, ammonia level reduction in plasma circulation, and AE between patients with creatinine clearance (CLcr) ≤35 mL/min and CLcr >35 mL/min in the Study 3 were conducted. CLcr of 35 mL/min was chosen as a cut-off value in order to have relatively sufficient sample size for the group with relatively worse renal function.

Results

Pharmacokinetics of PAA

PAA demonstrated nonlinear PK with greater than dose-proportional increase in both $C_{max}$ and AUC from 10 g/4 h or 20 g/24 h up in both healthy subjects and subjects with stable cirrhosis. The geometric mean of half-life for PAA increased from 0.65 hour to 5.99 hour when increasing dose from 3 g/4 h to 30 g/4 h; and from 1.25 hour to 4.09 hour when increasing dose from 30 g/24 h to 60 g/24 h. Plasma concentrations of PAGN peaked with a slightly delayed as compared to PAA peak concentration, confirming a rapid formation of PAGN. Urinary recovery of PAGN was similar when equivalent doses were administered over 4 hours or 24 hours of infusion. Recovered PAA as unchanged compound in urine counted <1% of the administered dose of PAA.

PAA plasma exposure showed noticeable difference among healthy Caucasian, Chinese, and Japanese subjects.

Hepatic impairment also altered PAA plasma exposure. To identify the factors contributing to PAA plasma exposure, population PK modeling was conducted. A one-compartment model with Michaelis-Menten kinetics describing the formation of PAGN from PAA adequately quantified PAA plasma concentration profiles in healthy subjects and patients. Body weight was identified as a significant covariate for the PK of PAA in both healthy subjects and patients. Other factors such as ethnicity and hepatic/renal impairment on the PK of PAA are described below.

Hepatic and Renal Dysfunction on PAA PK

Observed steady state PAA concentrations in patients with various hepatic dysfunction in Study 3 revealed that plasma PAA concentration at steady state (during infusion period) was approximately 35% higher in Child-Pugh C (C-P C) patients than that of Child-Pugh B (C-P B) patients following the administration of 15 g/24 h. Population PK modeling conducted on the patient population (Studies 2 and 3) confirmed that in addition to the body weight, hepatic impairment was another significant covariate that altered PAA plasma exposure. Therefore, relative to a patient with the same body weight, a patient with Child-Pugh C would be exposed to PAA at steady state 36% higher than that of a patient with Child-Pugh B. Mild, moderate, or severe renal dysfunction on PAA PK was evaluated through population PK analysis with the datasets of Studies 2, 3 and 5. Renal dysfunction had insignificant impact on the exposure of PAA. In Study 5, the mean dose normalized PAA exposure ($C_{max}$ and $AUC_t$) was 2.61 μg/mL/g and 54.9 μg*h/mL/g for the subjects with normal renal function and 1.58 μg/mL/g and 45.4 μg*h/mL/g for subjects with severely impaired renal function, respectively. In addition, the mean dose normalized baseline corrected ORN exposure ($C_{max}$ and $AUC_{0-inf}$) was lower for the subjects with normal renal function than subjects with severely impaired renal function (2.09 μg/mL/g and 64.1 μg*h/mL/g vs 2.28 μg/mL/g and 80.3 μg*h/mL/g, respectively).

Since PAGN is near 100% excreted from urine, renal dysfunction is expected to increase PAGN plasma exposure. In the severe renal impairment study, though the dose was reduced by 53% for the severe renal impairment group, PAGN plasma exposure ($C_{max}$ and AUC) was much higher than those in the normal renal function group. Specifically, the mean dose normalized PAGN exposure ($C_{max}$ and $AUC_t$) was lower for the subjects with normal renal function compared to subjects with severely impaired renal function (3.35 μg/mL/g and 69.9 μg*h/mL/g vs 16.1 μg/mL/g and 383 μg*h/mL/g, respectively). Compared to normal renal function subjects having a renal clearance of 24.5 L/h, the mean renal clearance of PAGN for severe renal impairment subjects was substantially lower at about 4.66 L/h. In Study 3, the lowest creatinine clearance at baseline was 28.7 mL/min There were nine subjects with baseline creatinine clearance between 28.7 to 35 mL/min. Out of those nine subjects, six had Child Pugh score C, two with Child Pugh score B, and one with Child Pugh score A. The distribution of C-P C patients in this subgroup (67%) was similar to the subgroup with baseline creatinine clearance >35 mL/min (66%).

FIG. 1 shows the observed PAA, PAGN and ammonia plasma exposures for the renal impaired group having a baseline creatinine clearance level of less than 35 mL/min (a, b and c) as compared to the group having a baseline creatinine clearance level of greater than 35 mL/min (d, e and f) in Studies 2, 3 and 5. The results suggest that no difference in PAA plasma concentrations between the two groups was observed. However, plasma exposure of PAGN was clearly higher and showed continue accumulation in those patients with CLcr ≤35 mL/min. While PAGN plasma exposure was elevated, ammonia reduction of the two subgroups were comparable, suggesting that reduced PAGN excretion did not translate to ammonia removal from plasma circulation and severe renal dysfunction showed no impact on the elimination of PAA.

Ethnicity on PAA PK

The results from Study 4 revealed that the PK difference between Chinese and Japanese was rather attributed to the difference in body weight (74.2 kg of Chinese vs. 56.7 kg of Japanese) and unbalanced gender distribution (all males in the Chinese arm vs. 25% of males in the Japanese arm). It was worth noting that gender only contributed to the volume of distribution of PAA but not clearance of PAA. This indicated that steady state plasma PAA exposure would be comparable for both gender, if the male and female subjects were having the same body weight. This conclusion was applicable to the Caucasian vs. Asian group too, when expanding the analysis to Caucasian population. In short, the observed PK difference in healthy subjects across ethnic groups was due to the difference in body weight and unbalanced gender distribution rather than in genetic polymorphisms of P450s. Since gender difference was not statistically significant in patients with stable cirrhosis or HE patients, body weight and hepatic insufficiency will be the two important factors to determine the dosing regimen in Asian HE patients.

Safety/Tolerability

In Study 1 of healthy subjects, LOPA treatment related TEAEs in the SAD portion included headache (22 subjects), dizziness postural (10 subjects), nausea (12 subjects), somnolence (8 subjects), tinnitus (7 subjects), vomiting (6 subjects), and dizziness (4 subjects). In the MAD portion of the study, LOPA related TEAEs included headache (5 subjects), somnolence (4 subjects), and tinnitus (4 subjects); all were reported with the 20 g/4 hours regimen. There were no clinically significant abnormal laboratory parameters and there were no deaths or other SAEs during the study. Doses of 10 g/4 hours and below were well tolerated. Dosing with 24 hours of infusion appeared to be a preferred regimen due to tolerability.

In the single dose 20 g/24 h study of healthy Chinese and Japanese, no clinically significant findings in laboratory parameters, vital signs, physical examinations, or ECGs were observed. The only TEAE possibly related to study drug was mild nausea in one Japanese subject, and was consistent with gastrointestinal AEs of nausea reported in healthy subjects in other LOPA studies.

In Study 2 of patients with stable cirrhosis, LOPA was well tolerated up to 20 g/4 hours, or 40 g with 24-hour infusion. LOPA related TEAEs in the 40 g/24 hours cohort included headache, somnolence, and restlessness.

In Study 3 of hospitalized patients with cirrhosis and acute episode of HE, majority of patients (62.3%) who experienced TEAEs had events that were at most mild or moderate in severity. No clinically significant differences in the percentage of patients with TEAEs were observed across LOPA dose groups and placebo. A total of 26 patients (15 placebo, 11 LOPA) died during the study. The death rates for LOPA and placebo were 24% versus 26% for 10 g/24 hours, 5% versus 12% for 15 g/24 hours, and 4% versus 0% for 20 g/24 hours, respectively.

In Study 5, single 7 g or 15 g doses of LOPA were well tolerated by all subjects with severe renal impairment or matched normal renal function, respectively, and no subject discontinued the study. No LOPA related to TEAEs were reported. All AEs were mild and there were no subjects who experienced serious AEs, dose interruptions due to AEs, drug withdrawn due to AE, or AEs leading to death.

Exposure of PAA and CNS AE Relationship

Figure 2:
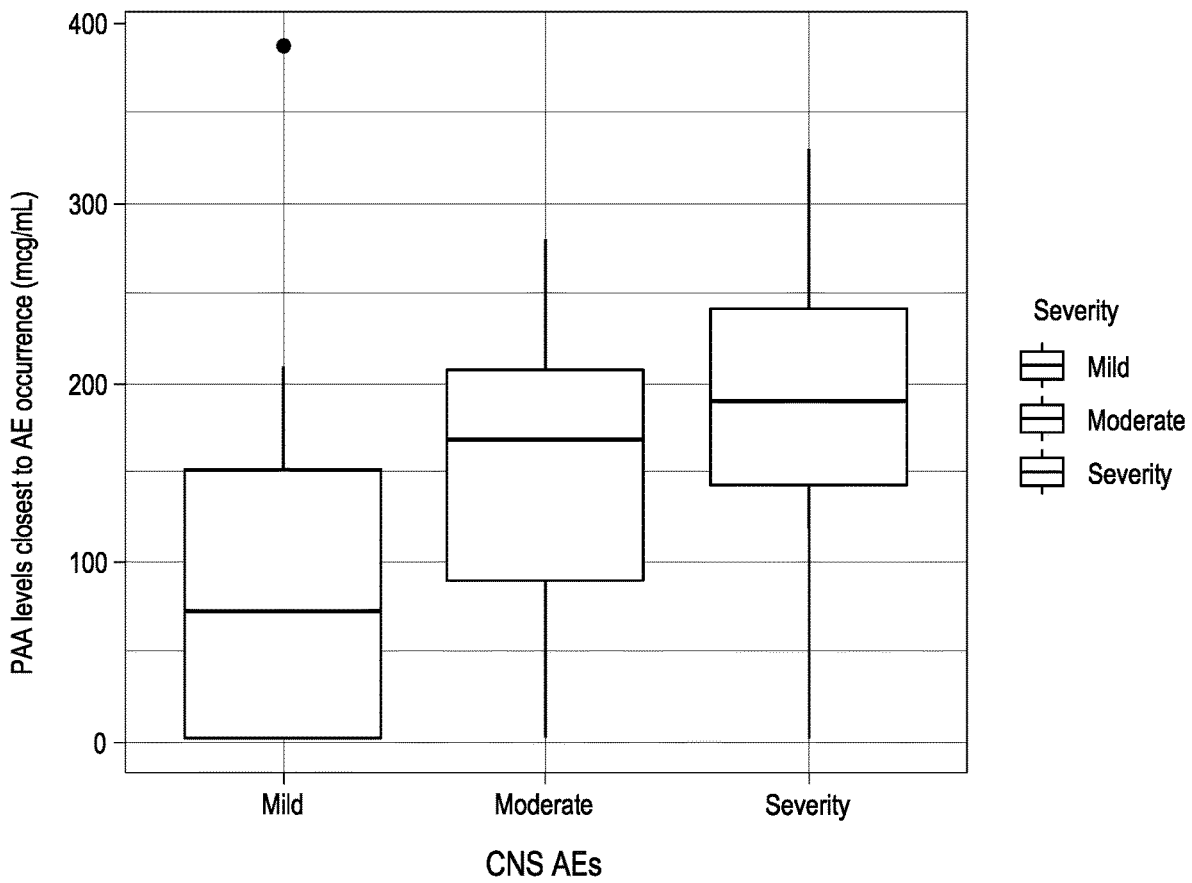
FIG. 2 shows the correlation between the adverse events (AEs) and PAA plasma concentrations in healthy subjects (Study 1 described in Example 2).

Study 1 reported 36 CNS AEs from 29 healthy subjects in the safety population that were considered to be related to study drug by the investigators. Sixteen of the 36 drug-related CNS AEs had a reported severity of moderate to severe; 32 of 36 drug-related CNS AEs (89%) occurred earlier than 8 hours after the start of study drug infusion. In this population of healthy subjects, the severity of the CNS AEs appeared to be correlated to PAA plasma concentrations, as shown in FIG. 2.

Figure 3:
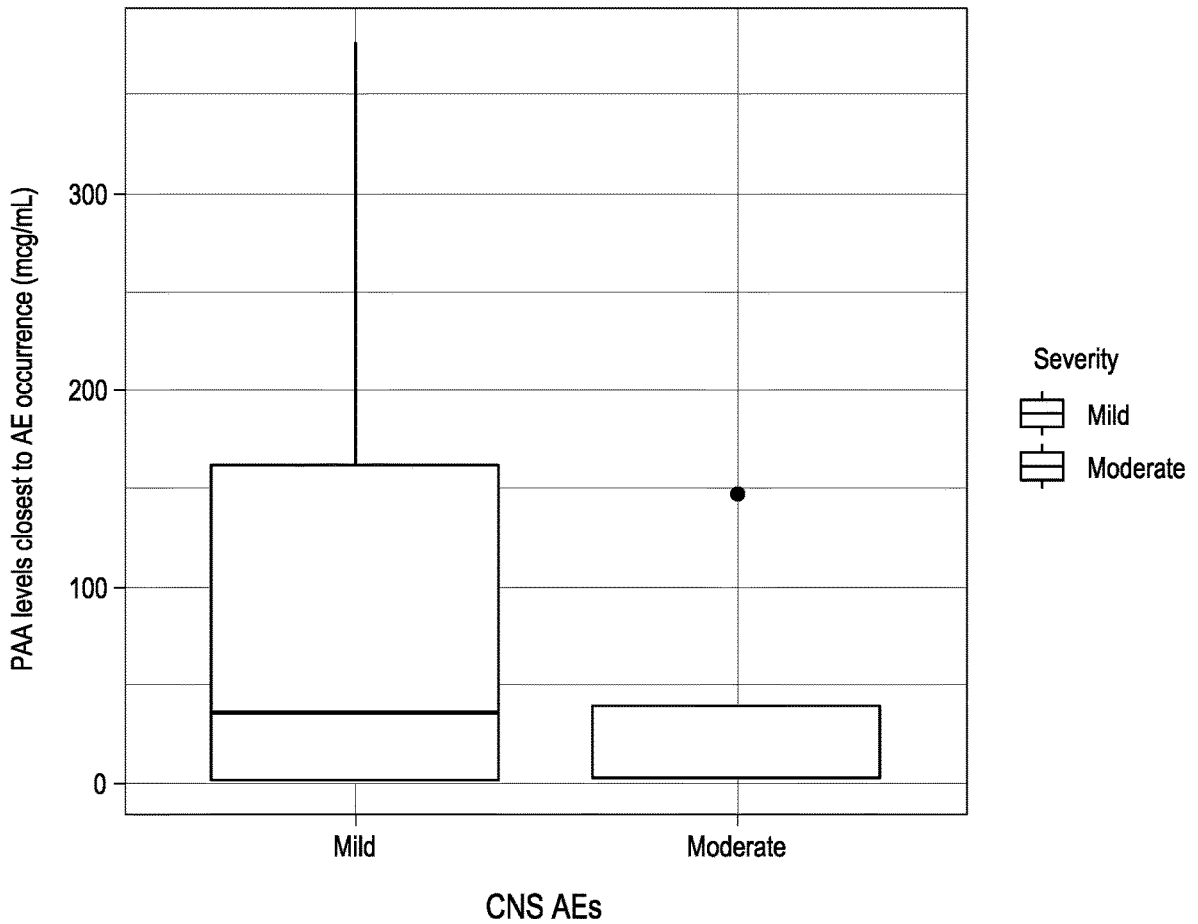
FIG. 3 shows the correlation between the adverse events (AEs) and PAA plasma concentrations in patients with chronic liver disease (cirrhosis) (Study 2 described in Example 2).

Of the 43 patients in the safety population of Study 2, 35 received LOPA and 8 received placebo. Fourteen subjects receiving LOPA experienced a CNS AE, 10 of which were of mild in severity; none of the events was reported as severe. No correlation between PAA concentrations and CNS AE occurrence was observed, as shown in FIG. 3.

Eleven of the 226 (4.87%) patients in the safety population of Study 3 experienced a CNS-related AE. Of these 11 patients, 8 received placebo and 3 received LOPA. All 3 patients treated with LOPA were Child-Pugh C patients and experienced one occurrence of mild headache during treatment. Time to the AE ranged from approximately 29 to 43 hours after the start of study drug infusion. PAA concentrations ranged from approximately 91 to 109 mcg/mL before the event and from 123 to 238 mcg/mL after the event. The median concentrations of PAA at steady state for all Child-Pugh C patients treated with LOPA in the study were 118 μg/mL (ranged from 11.4 to 223 mcg/mL) and 120 μg/mL (ranged from 7.15 to 454 mcg/mL) for patients in the 10 g/24 hr (n=23) and 15 g/24 hr (n=38) dose groups, respectively. Thus, the PAA concentrations around the time of the CNS AEs were generally around the median.

Overall, the correlation between PAA concentrations and CNS AEs appears to vary across populations. In healthy subjects, severity of CNS AEs increased with plasma PAA concentration. However, such correlation was not observed in patients with stable cirrhosis, or in hospitalized patients with liver cirrhosis, hyperammonemia, and an acute episode of hepatic HE.

PAGN Exposure with AEs

Nine patients with CLcr ≤35 mL/min in Study 3 experienced much higher PAGN levels and continued to accumulate PAGN during the 5 days of infusion. Three of the nine patients experienced possible drug-related AEs. However, none of the AEs was deemed serious. The AE data suggests that high PAGN plasma concentrations due to worse renal function were not attributable to AE profiles.

Discussion

The fact that reduced PAGN excretion had no impact on PAA exposure and ammonia level reduction in plasma circulation confirmed that the formation of PAA to PAGN is an irreversible process, and therefore, elevated PAGN plasma concentration will not alter the rate of conjugation of PAA to glutamine.

In hospitalized patients with hyperammonemia and an acute episode of HE, no LOPA related hepatotoxicity, or renal function decline was observed. No PAA exposure related neurotoxicity was observed either. The odds of experiencing a neurological AE did not increase with elevated PAA concentration in UCD or HE patients. Therefore, PAA threshold values from other populations (e.g., the 500 μg/mL threshold for oncology patients) may differ and should not be extrapolated to patients with chronic liver disease (cirrhosis) and HE.

In summary, the various study results suggest that PAA exposure was not correlated to neurologic AEs in HE patients. Body weight/body surface area significantly impacted the PK of PAA prodrugs and supports body size based dosing. If a flat dose LOPA is chosen, attention should be paid to those patients with low body weight and severe hepatic impairment. Though renal impairment significantly increases PAGN plasma exposure, it has relatively little impact on the AEs and plasma ammonia level.

Example 3

In this example, aqueous solutions comprising L-ornithine phenylacetate at different concentrations and various pHs were prepared, tested and evaluated for long term storage stability.

Solubility and pH

In an initial study, the solubility of a 400 mg/mL concentration of LOPA was evaluated at pH's of 5.0, 5.1, 5.2, 5.3 and 5.4. The pH of the LOPA solutions were adjusted with the addition of concentrated HCl, dissolution was performed at room temperature and stored at 2-8° C. It was found that pH's above 5.4 at 5° C. avoided precipitation of LOPA, wherein varying amounts of crystallization were found in all samples below pH 5.4 and increased crystallization was observed as the pH of the sample decreased.

In a follow-on study, the solubility of LOPA was investigated at various pH's at room temperature and 5° C., and the results are shown in Table 5 below. The pH of the LOPA solutions were adjusted with the addition of citric acid, and the solutions were mixed for 24 hours.

TABLE 5

|  | LOPA Solubility | | |
| --- | --- | --- | --- |
| Sample | PAA Concentration (mg/mL) | Ornithine Concentration (mg/mL) | LOPA Concentration (mg/mL) |
| pH 4, RT | 27.4 | 221.4 | 248.8 |
| pH 4.5, RT | 32.4 | 225.5 | 257.9 |
| pH 5, RT | 356.8 | 360.2 | 717.0 |
| pH 5.5, RT | 240.6 | 239.0 | 479.6 |
| pH 6, RT | 216.2 | 215.4 | 431.6 |
| (control), RT | 192.5 | 189.1 | 381.6 |
| pH 4, 5° C. | 9.3 | 206.3 | 215.7 |
| pH 4.5, 5° C. | 18.3 | 217.2 | 235.5 |
| pH 5, 5° C. | 44.6 | 218.5 | 263.1 |
| pH 5.5, 5° C. | 212.4 | 209.1 | 421.5 |
| pH 6, 5° C. | 181.1 | 181.6 | 362.7 |
| (control), 5° C. | 183.2 | 184.6 | 367.8 |

As shown in Table 5, the probability of precipitation for 400 mg/mL concentration of LOPA is relatively higher than for 300 mg/mL concentration if pH is below 5.5 at 5° C.

Based on the DOE Stability Study results (up to 6 months), the only stability indicating impurity observed was 3-amino-2-piperidone, the lactam impurity of L-Ornithine. It appeared that the main driving factor in formation of ornithine lactam is pH, with lactam formation slowed at lower pH values in accelerated temperature conditions whereas long term storage at 5° C. did not show any significant change in lactam impurities. Lactam levels from refrigerated samples did not rise above a level of 0.05% w:w relative to nominal concentration of ornithine. Clinical batch stability study at long term storage did not show any increase in related substances until about 9 months.

Example 4

In this example, a cross-sectional cohort-based analysis of the prevalence of hepatic encephalopathy (HE) in the U.S.

general population based on anonymized patient level data (APLD). In particular, patients diagnosed with cirrhosis in the APLD data set within 1 year of cirrhosis diagnosis were used to deduce the prevalence of HE within the data set and estimate the number of patients with HE in the US general population the 1 year period prevalence (hereafter the "prevalence"). In addition, de-identified patient diagnostic laboratory data was used to match HE events to serum ammonia level laboratory data.

Subjects

The cirrhosis prevalence analysis included adult patients (≥18 years) within the APLD database with medical-claim or hospital-claim activity and an International Classification of Disease (ICD), ninth and tenth revisions, clinical modification (ICD-9-CM ICD-10-CM) diagnosis code for cirrhosis. For the HE prevalence analysis, adult patients (≥18 years of age) within the APLD database were identified if they had a first cirrhosis diagnosis within a 24 month time frame 1 year prior to the start of the observation period (12 months period). The index date was defined as the earliest date of cirrhosis diagnosis within the observation period. Patients were required to have at least 12 months of claims pre-index date to ensure they were newly diagnosed. Patients were excluded from the analysis if they had a diagnosis code for HE prior to the index date or had claims activity in fewer than 2 quarters of the observation period. In the resulting cirrhosis analysis cohort, the number of prevalent cases of HE ICD-9-CM and ICD-10-CM codes within 1 year of cirrhosis diagnosis (index date) was analyzed during the observation period.

Real-world, patient-level, diagnostic laboratory data was used to assess the distribution of ammonia levels within identified patients with HE. Serum ammonia values were identified for the subset of patients with an HE diagnosis claim used in the prevalence analysis. Laboratory data were merged back to the APLD data using unique patient identifiers to describe patients (≥18 years) with serum ammonia levels measured during or within ±2 days of a recorded HE event.

To ensure laboratory data were reflective of the disease severity for the larger HE patient population, the number of HE events was compared between the laboratory data set and the APLD data. The HE cohort in the APLD database was defined as all patients with first HE diagnosis (index date: 2 years prior to the start of the observation period), and the number of events was defined by looking at a longitudinal duration starting 2 years prior to the index date and ending 2 years following the index date. The laboratory cohort included patients with HE that had serum ammonia level data measured within ±2 days of an HE event.

Statistical Analysis

Counts of patients were aggregated by medical or hospital claim into age groups (18-25, 26-34, 35-44, 45-64, ≥65 years) in the cirrhosis prevalence analysis. Prevalence of HE within patients with cirrhosis was calculated by dividing the number of patients with an HE diagnosis code by the number of patients with a first cirrhosis diagnosis code. The resulting HE prevalence was then applied to the estimated number of US cirrhosis patients to calculate the subpopulation of patients with HE. To analyze the distribution of ammonia levels in patients with HE, the proportion of patients with HE was reported for pre-specified serum ammonia level groups.

Results

Overall 272,256 patients with cirrhosis claims were identified from the APLD database. Cirrhosis patients in the analysis were most likely to be aged 45 to 64 years, male (54%), and have Medicare coverage (52%). The prevalence was highest in individuals 45 to 64 years of age (0.56% and 0.29%, respectively). Accounting for the source data, the weighted sum of the number of patients with cirrhosis in the United States in the 1 year observation period was 536,856, resulting in a prevalence of 0.21%.

Within the APLD database, it was determined that 37.6% (n=37,214) of those patients with cirrhosis had a diagnosis of HE within 1 year of their respective index date of cirrhosis diagnosis. This proportion applied to the estimated number of patients with cirrhosis in the United States resulted in a prevalence estimate of 201,858 cirrhosis patients with HE in the observation period.

Figure 4:
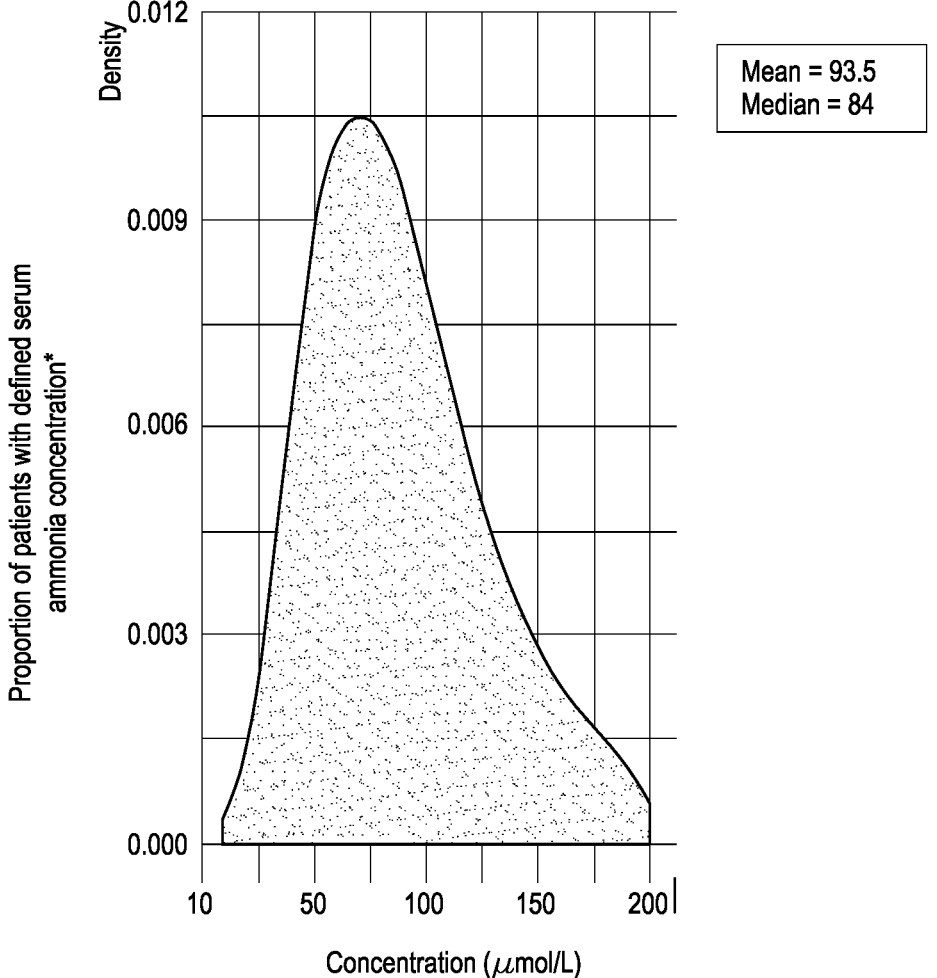
FIG. 4 illustrates the serum ammonia distribution in cirrhotic patients in a study described in Example 4.

Within 11,113 patients with HE who were identified as having serum ammonia data, serum ammonia levels exhibited a mean concentration of 93.5 μmol/L, shown in FIG. 4. Fewer than 200,000 cirrhosis patients with HE were estimated to have a serum ammonia level greater than 21 μmol/L (n=196,191).

TABLE 6

Serum Ammonia Levels in Patients With HE

| Serum Ammonia Concentration Range (μmol/L) | Number of Patients (%) With Serum Ammonia | | Cumulative Estimated Number of Patients With Serum Ammonia ≥ Corresponding Concentration |
|---|---|---|---|
| | ≤Corresponding Concentration Range | >Corresponding Concentration Range | Range in the observation period* |
| 0-10 | 6 (0.05) | 11,107 (99.9) | 201,749 |
| 11-20 | 48 (0.43) | 11,059 (99.5) | 200,877 |
| 21-30 | 258 (2.32) | 10,801 (97.2) | 196,191 |
| 31-40 | 563 (5.07) | 10,238 (92.1) | 185,964 |
| 41-50 | 879 (7.91) | 9359 (84.2) | 169,998 |
| 51-60 | 1088 (9.79) | 8271 (74.4) | 150,235 |
| 61-70 | 1127 (10.14) | 7144 (64.3) | 129,764 |
| 71-80 | 1153 (10.38) | 5991 (53.9) | 108,821 |
| 81-90 | 1102 (9.92) | 4889 (44.0) | 88,804 |
| 91-100 | 939 (8.45) | 3950 (35.5) | 71,748 |
| 101-110 | 794 (7.14) | 3156 (28.4) | 57,326 |
| 111-120 | 628 (5.65) | 2528 (22.7) | 45,919 |
| 121-130 | 548 (4.93) | 1980 (17.8) | 35,965 |
| 131-140 | 411 (3.70) | 1569 (14.1) | 28,500 |
| 141-150 | 332 (2.99) | 1237 (11.1) | 22,469 |
| 151-160 | 277 (2.49) | 960 (8.6) | 17,438 |
| 161-170 | 203 (1.83) | 757 (6.8) | 13,750 |
| 171-180 | 192 (1.73) | 565 (5.1) | 10,263 |
| 181-190 | 141 (1.27) | 424 (3.8) | 7702 |
| 191-200 | 97 (0.87) | 327 (2.9) | 5940 |
| Total | 11,113 | N/A | N/A |

*Percentage of patients with levels greater than or equal to the corresponding range × the total number of cirrhosis patients with HE in the observation period, estimated as N = 201,858.
HE = hepatic encephalopathy; N/A = not applicable.

Discussion

This analysis offers a unique step-wise approach to HE prevalence estimation for the general public in the United States. Previous studies on liver cirrhosis prevalence did not evaluate the prevalence of HE in the US general population. This study demonstrates a 37.6% prevalence of HE in patients with cirrhosis, which translates to an estimated 201,858 patients with cirrhosis and HE in the observation period. When merged with laboratory data, approximately 196,000 patients with HE had a serum ammonia level greater than 21 μmol/L. An association between the prevalence of HE and ammonia levels is an unexpected and advantageous result of the study.

What is claimed is:

1. A method of treating or ameliorating hyperammonemia in a patient with liver disease, comprising:
administering a first amount of ornithine phenylacetate to the patient during a first period of time; and
administering a second amount of ornithine phenylacetate to the patient during a second period of time;
wherein the first amount of ornithine phenylacetate is between about 10 g to about 30 g, and the second amount of ornithine phenylacetate is less than the first amount.

2. The method of claim 1, wherein the first period of time is from about 1 hour to about 10 hours, the second period of time is longer than the first period of time, and a total of the first period of time and the second period of time is from about 18 hours to 36 hours.

3. The method of claim 1, wherein the first amount of ornithine phenylacetate is about 20 g, and wherein the first period of time is about 6 hours.

4. The method of claim 1, wherein the second amount of ornithine phenylacetate is about 15 g, and wherein the second period of time is about 18 hours.

5. The method of claim 1, wherein the second amount of ornithine phenylacetate is administered immediately after the completion of the administration of the first amount of ornithine phenylacetate.

6. The method of claim 1, wherein the first amount or the second amount of ornithine phenylacetate is administered by intravenous infusion.

7. The method of claim 1, further comprising administering a third amount of ornithine phenylacetate immediately following the completion of the administration of the second amount of ornithine phenylacetate during a third period of time, wherein the third period of time is from about 2 days to about 10 days.

8. The method of claim 7, wherein the third period of time is about 4 days.

9. The method of claim 7, wherein the third amount of ornithine phenylacetate administered per day (24 hours) is the same or less than the second amount of ornithine phenylacetate.

10. The method of claim 9, wherein the third amount of ornithine phenylacetate administered per day is about 15 g, and wherein the third amount of ornithine phenylacetate is administered by intravenous infusion.

11. The method of claim 1, wherein the patient is also receiving standard of care.

12. A method of treating or ameliorating hyperammonemia in a patient with liver disease, comprising:
selecting a patient with liver disease in need of treatment of hyperammonemia who is suffering from impaired renal function, wherein said patient has estimated glomerular filtration rate (eGFR) between 15 mL/min/1.73 m² and 29 mL/min/1.73 m²;
administering a first amount of ornithine phenylacetate to the patient during a first period of time; and
administering a second amount of ornithine phenylacetate to the patient during a second period of time;
wherein the first amount of ornithine phenylacetate is between about 5 g to about 20 g, and the second amount of ornithine phenylacetate is less than the first amount.

13. A method of treating or ameliorating hyperammonemia in a patient with liver disease, comprising:

determining the renal function or receiving information on the renal function of a patient with liver disease who is in need of treatment of hyperammonemia; and administering a first amount of ornithine phenylacetate to the patient during a first period of time; wherein the first amount is from about 10 g to about 30 g when the patient's estimated creatinine clearance is greater than 35 mL/min; or administering a first amount of ornithine phenylacetate to the patient during a first period of time; wherein the first amount is from about 5 g to about 15 g when the patient's estimated creatinine clearance is equal to or less than 35 mL/min.

14. A method of treating or ameliorating hyperammonemia in a patient with liver disease, comprising:

determining the body weight or body size or receiving information on the body weight or body size of a patient with liver disease who is in need of treatment of hyperammonemia;

administering a first amount of ornithine phenylacetate administered to the patient during a first period of time;

monitoring plasma concentration of phenylacetic acid in the patient; and adjusting the amount of ornithine phenylacetate administered to the patient during a second period of time based on the plasma concentration of phenylacetic acid.

15. A method of treating or ameliorating hyperammonemia in a patient with liver disease, comprising:

determining the degree of hepatic impairment or receiving information on the degree of hepatic impairment of a patient with liver disease who is in need of treatment of hyperammonemia;

administering a first amount of ornithine phenylacetate administered to the patient during a first period of time;

monitoring plasma concentration of phenylacetic acid in the patient; and adjusting the amount of ornithine phenylacetate administered to the patient during a second period of time based on the plasma concentration of phenylacetic acid.

16. The method of claim 1, further comprising measuring a serum ammonia level of the patient prior to administering the first amount of ornithine phenylacetate to the patient.

17. The method of claim 16, wherein the serum ammonia level of the patient is ≥21 μmol/L.

18. The method of claim 1, wherein the patient has cirrhosis.

19. The method of claim 1, wherein the patient is at risk of hepatic encephalopathy or has had at least one episode of hepatic encephalopathy, or the patient is hospitalized due to one or more hepatic encephalopathy episodes.

20. The method of claim 1, wherein the patient has received at least 4 hours to 6 hours of standard of care prior to the administration of the first amount of ornithine phenylacetate.

21. The method of claim 1, wherein ornithine phenylacetate is administered as an aqueous solution comprising about 200 mg/mL to about 400 mg/mL ornithine phenylacetate.

22. A pharmaceutical formulation comprising an aqueous solution of about 200 mg/mL to 400 mg/mL of ornithine phenylacetate and at least one pH adjusting agent, wherein the aqueous solution has a pH range of about 5.4 to about 6.5.

23. A method of treating or ameliorating hyperammonemia in a patient with liver disease, comprising administering a first amount of ornithine phenylacetate to the patient during a first period of time and administering a second amount of ornithine phenylacetate to the patient during a second period of time, wherein:

(A) (i) the first amount of ornithine phenylacetate is 20 g and the first period of time is 6 hours; and (ii) the second amount of ornithine phenylacetate is the same or less than 20 g and the second period of time is 18 hours; or (B) if the patient in need of treatment of hyperammonemia is suffering from hepatic impairment and/or has a body weight of <50 kg;

(i) the first amount of ornithine phenylacetate is 15 g and the first period of time is 6 hours; and (ii) the second amount of ornithine phenylacetate is the same or less than 15 g and the second period of time is 18 hours;

wherein the first and second amounts of ornithine phenylacetate are administrable by intravenous infusion.

24. The method of claim 23, wherein a further third amount of ornithine phenylacetate is administered during a third period of time, wherein the third period of time is for up to 4 days and wherein:

(i) the third amount of ornithine phenylacetate administered per day (24 hours) is the same or less than 15 g; or (ii) if the patient in need of treatment of hyperammonemia is suffering from hepatic impairment and/or has a body weight of <50 kg, the third amount of ornithine phenylacetate administered per day (24 hours) is 10 g.

25. The method of claim 24, wherein the third period of time is about 4 days.

\* \* \* \* \*